United States Patent
Ichim et al.

(10) Patent No.: US 11,141,471 B2
(45) Date of Patent: Oct. 12, 2021

(54) UNIVERSAL DONOR CHECKPOINT INHIBITOR SILENCED/GENE EDITED CORD BLOOD KILLER CELLS

(71) Applicant: Regen Biopharma, Inc., La Mesa, CA (US)

(72) Inventors: Thomas Ichim, San Diego, CA (US); David Koos, La Mesa, CA (US); Harry Lander, La Mesa, CA (US)

( * ) Notice: Subject to any disclaimer, the term of this patent is extended or adjusted under 35 U.S.C. 154(b) by 167 days.

(21) Appl. No.: 15/494,358

(22) Filed: Apr. 21, 2017

(65) Prior Publication Data

US 2017/0304418 A1    Oct. 26, 2017

Related U.S. Application Data

(60) Provisional application No. 62/327,245, filed on Apr. 25, 2016.

(51) Int. Cl.
| | |
|---|---|
| *A61K 35/17* | (2015.01) |
| *A61K 35/51* | (2015.01) |
| *A61K 39/00* | (2006.01) |
| *C12N 5/0783* | (2010.01) |

(52) U.S. Cl.
CPC .......... *A61K 39/0011* (2013.01); *A61K 35/17* (2013.01); *A61K 35/51* (2013.01); *C12N 5/0646* (2013.01); *A61K 2039/5154* (2013.01); *A61K 2039/5156* (2013.01); *C12N 2501/125* (2013.01); *C12N 2501/2307* (2013.01); *C12N 2501/2315* (2013.01)

(58) Field of Classification Search
CPC .... A61K 39/0011; A61K 35/17; A61K 35/51; C12N 5/0634
USPC ...................................... 424/277.1
See application file for complete search history.

(56) References Cited

U.S. PATENT DOCUMENTS

| | | | |
|---|---|---|---|
| 2011/0002930 A1* | 1/2011 | Lum | A61K 39/001 424/136.1 |
| 2011/0236427 A1* | 9/2011 | Baier | C12N 15/1138 424/277.1 |

* cited by examiner

*Primary Examiner* — Yan Xiao
(74) *Attorney, Agent, or Firm* — Baumgartner Patent Law; Marc Baumgartner

(57) ABSTRACT

Disclosed are compositions of matters, cells, and treatment protocols useful for induction of anticancer responses in a patient suffering from cancer. In one embodiment the invention provides the use of NR2F6 silencing or gene editing in cord blood cells possessing anti-tumor activity in order to induce potentiated killer cells suitable for therapeutic use. In one embodiment said allogeneic cord blood killer cells are administered to initiate a cascade of antitumor immune responses, with initially responses mediated by allogeneic killer cells, and followed by endogenous immune responses.

13 Claims, No Drawings

UNIVERSAL DONOR CHECKPOINT INHIBITOR SILENCED/GENE EDITED CORD BLOOD KILLER CELLS

CROSS-REFERENCE TO RELATED APPLICATIONS

This application claims priority to U.S. Provisional Application No. 62/327,245, filed Apr. 25, 2016, which is incorporated herein by reference in its entirety.

FIELD OF THE INVENTION

The invention pertains to the field of cancer immunotherapy, more specifically, the invention relates to the use of cord blood cells as starting cell populations for generation of killer cells that possess selectivity to tumor tissue, more specifically, the invention relates to use of gene silenced/gene edited cord blood cells in which said gene silencing/gene editing enhances killer activity of said cord blood derived cells through enhancement of tumor cytotoxic function through silencing/gene editing of checkpoint inhibitors.

BACKGROUND OF THE INVENTION

Support for immunological control of neoplasia has come in many forms, ranging from animal studies in which the incidence of spontaneous cancer is substantially higher in mice lacking NK cell activity [1-4], to studies in which patients with higher tumor infiltrating lymphocytes possess longer survival [5-7]. Indeed it appears that in the cancer patient a "battle" is actually occurring between tumor-induced immune suppressive mediators, and immune responses attempting to clear the tumor from the host. For example, it is widely known that tumors induce the de novo generation of T regulatory cells. The natural function of these cells is to inhibit pathological autoimmunity. During development of self tolerance in the thymus, while conventional T cells are negatively deleted upon recognition of self-antigen, T regulatory cells that recognize self antigen are positively selected and promoted to expand by the body [8-10]. The fundamental importance of T regulatory cells is observed in animals lacking T regulatory cells through deletion of FoxP3, in which spontaneous multi-organ autoimmunity occurs, which is also observed in patients possessing a mutation in the gene encoding for the human homologue [11]. In cancer, tumors reprogram the immune system to generate T regulatory cells that serve to protect the tumor against immunological attack. Some examples of this will be listed below.

Jie et al examined patients with head and neck cancer treated with anti-EGFR antibody cetuximab. The frequency, immunosuppressive phenotype, and activation status of Treg and natural killer (NK) cells were analyzed in the circulation and tumor microenvironment of cetuximab-treated patients. The antibody treatment increased the frequency of CD4(+) FOXP3(+) intratumoral T regulatory cells. These T regulatory cells suppressed cetuximab-mediated antibody-dependent cellular cytotoxicity (ADCC) and their presence correlated with poor clinical outcome in two prospective clinical trial cohorts [12].

Hanakawa et al examined 34 patients with tongue cancer immunohistochemically for CD4, CD8, and Forkhead box P3 (Foxp3). Immunoreactive cells were counted in cancer stroma and nest regions, and relationships between cell numbers and disease-free survival rates were analyzed. They found by univariate analysis for disease-free survival that high-level infiltration of Tregs (CD4(+)Foxp3+) into both cancer nests and stroma and presence of helper T (CD4(+) Foxp3−) cells in cancer stroma as potential predictors of significantly worse prognosis. In early-stage cases (stage I/II), high-level infiltration of Tregs in cancer nests correlated significantly with poor disease-free survival rate [13].

Kim et al studied 72 patients with early stage (I to III) breast cancer and found increased number of Foxp3(+) Tregs was significantly correlated with tumors with lymph node metastasis (P=0.027), immunopositivity for p53 (P=0.026), and positive for Ki-67 (P<0.001). There were significant correlations between the increased Foxp3(+) Treg/CD4(+) T-cell ratio and lymph node metastasis (P=0.011), the expression of ER (P=0.023), and immunopositivity of p53 (P=0.031) and Ki-67 (P=0.003). Of note, lower Foxp3(+) Treg/CD4(+) T-cell ratio was significantly associated with triple-negative breast cancer (P=0.004) [14].

A means of overcoming immune suppression in cancer is by blocking inhibitory signals generated by the tumor, or generated by cells programmed by the tumor. In essence, all T cells possess costimulatory receptors, such as CD40, CD80 and CD86, which are also known as "signal 2". In this context, Signal 1 is the MHC-antigen signal binding to the T cell receptor, whereas signal 2 provides a costimulatory signal to allow for the T cells to produce autocrine IL-2 and differentiate into effector and memory T cells. When T cells are activated in absence of signal 2 they become anergic or differentiate into Treg cells. The costimulatory signals exist as a failsafe mechanism to prevent unwanted activation of T cells in absence of inflammation. Indeed, most of the inflammatory conditions associated with pathogens are known to elicit signal 2. For example, viral infections activate toll like receptor (TLR)-3, 7, and 8. Activation of these receptors allows for maturation of plasmacytoid dendritic cells which on the one hand produce interferon alpha, which upregulates CD80 and CD86 on nearby cells, and more directly, the activation of these TLRs results in the plasmacytoid dendritic cell upregulating costimulatory signals. In the case of Gram negative bacteria, upregulation of signal 2 is mediated by LPS binding to TLR-4 which causes direct maturation of myeloid dendritic cells and thus expression of CD40, CD80 and CD86, as well as production of cytokines such as IL-12 and TNF-alpha, which stimulate nearby cells to upregulate signal 2.

Once immune responses have reached their peak, coinhibitory receptors start to become upregulated in order to suppress an immune response that has already performed its function. This is evidenced by upregulation of coinhibitory molecules on T cells such as CTLA4, PD-1, TIM-3, and LAG-3. The finding of co-inhibitory receptors has led to development of antibodies against these receptors, which by blocking their function allow for potent immune responses to ensure unrestrained. The advantage of inhibiting these "immunological checkpoints" is that they not only allow for T cell activation to continue and to not be inhibited by Treg cells, but they also allow for the T cell receptor to become more promiscuous. By this mechanism T cells start attacking various targets that they were not programmed initially to attack.

The currently approved checkpoint inhibitors, which block CTLA-4 and PD-1, great clinical progress has been achieved in comparison to previous treatments that were available. In the example of CTLA-4 inhibition ipilimumab has been approved by regulators and tremelimumab is in advanced stages of clinical trials. Although these anti-CTLA-4 antibodies have modest response rates in the range of 10%, ipilimumab significantly improves overall survival, with a subset of patients experiencing long-term survival benefit. In a phase III trial, tremelimumab was not associated with an improvement in overall survival. Across clinical trials, survival for ipilimumab-treated patients begins to separate from those patients treated in control arms at around 4-6 months, and improved survival rates are seen at 1, 2, and 3 years. Further, in aggregating data for patients treated with ipilimumab, it appears that there may be a plateau in survival at approximately 3 years. Thereafter, patients who remain alive at 3 years may experience a persistent long-term survival benefit, including some patients who have been followed for up to 10 years.

In the case of PD-1 inhibition, Herbst et al. [15] evaluated the single-agent safety, activity and associated biomarkers of PD-L1 inhibition using the MPDL3280A, a humanized monoclonal anti-PD-L1 antibody administered by intravenous infusion every 3 weeks (q3w) to patients with locally advanced or metastatic solid tumors or leukemias. Across multiple cancer types, responses as per RECIST v1.1 were observed in patients with tumors expressing relatively high levels of PD-L1, particularly when PD-L1 was expressed by tumor-infiltrating immune cells. Specimens were scored as immunohistochemistry 0, 1, 2, or 3 if <1%, ≥1% but <5%, ≥5% but <10%, or ≥10% of cells per area were PD-L1 positive, respectively. In the 175 efficacy-evaluable patients, confirmed objective responses were observed in 32 of 175 (18%), 11 of 53 (21%), 11 of 43 (26%), 7 of 56 (13%) and 3 of 23 (13%) of patients with all tumor types, non-small cell lung cancer (NSCLC), melanoma, renal cell carcinoma and other tumors (including colorectal cancer, gastric cancer, and head and neck squamous cell carcinoma). Interestingly, a striking correlation of response to MPDL3280A treatment and tumor-infiltrating immune cell PD-L1 expression was observed. In summary, 83% of NSCLC patients with a tumor-infiltrating immune cell IHC score of 3 responded to treatment, whereas 43% of those with MC 2 only achieved disease stabilization. In contrast, most progressing patients showed a lack of PD-L1 upregulation by either tumor cells or tumor-infiltrating immune cells.

The first widespread utilization of cord blood as a stem cell source was in the treatment of pediatric hematological malignancies after myeloablative conditioning. Since matching requirements for this type of transplant are not as strict as for hematopoietic stem cell sources, cord blood began gaining acceptance in adult patients lacking bone marrow donors [16-21]. Outside the area of oncology, the clinical use of cord blood has expanded into various areas that range from reconstituting a defective immune system [22], to correcting congenital hematological abnormalities [23], to inducing angiogenesis [24]. To our knowledge cord blood has not been used in an allogeneic setting following gene silencing/gene editing of immunological checkpoints.

Although progress has been made in extending patient's lives, significant hurdles exist in terms of the patients that do not respond to therapy, or where responses are short lived. We overcome these limitations by administering allogeneic cord blood derived cells have been gene silenced or permanently gene edited so as to not succumb to tumor inhibition. Furthermore, in one embodiment of the invention, the lymphocytes that have been gene edited possess a suicide gene, which allows for destruction of the modified lymphocytes should autoimmunity or pathological consequences arise.

DESCRIPTION OF THE INVENTION

The invention provides means of inducing cancer killing lymphoid cells through expansion and differentiation of cord blood derived progenitor cells together with gene silencing or gene editing of lymphocytes derived from umbilical cord blood. In one embodiment of the invention lymphocytes derived from umbilical cord blood are gene silenced or gene edited to reduce, or completely abolish expression of checkpoint inhibitor genes. Described herein are compositions and methods for gene editing of checkpoint genes. Essentially, the invention teaches the application of gene editing technology as a means of generating lymphocytes resistant to inhibitory signals. Furthermore, the invention teaches the use of suicide genes to allow for deletion of manipulated lymphocytes administered to the host. Means of inducing the process of gene deletion are known in the art. Original notion that gene editing may be feasible was provided by Barrangou et al. [25] who showed that clustered regularly interspaced short palindromic repeats (CRISPR) are found in the genomes of most Bacteria and Archaea and after bacteriophage challenge, the bacteria integrated new spacers derived from phage genomic sequences. Removal or addition of particular spacers modified the phage-resistance phenotype of the cell. They concluded that CRISPR, together with associated cas genes, provided resistance against phages, and resistance specificity is determined by spacer-phage sequence similarity. These techniques, which are incorporated by reference provided a clue that editing or deleting DNA segments may be possible. In 2013, Mali et al took the observations that bacteria and archaea utilize CRISPR and the CRISPR-associated (Cas) systems, combined with short RNA to direct degradation of foreign nucleic acids, and applied the concept to gene-editing of human cells. They developed a type II bacterial CRISPR system to function with custom guide RNA (gRNA) in human cells. They used the system to delete the human adeno-associated virus integration site 1 (AAVS1). They obtained targeting rates of 10 to 25% in 293T cells, 13 to 8% in K562 cells, and 2 to 4% in induced pluripotent stem cells [26]. Subsequent variations on the theme were reported, which were effective at deleting human genomic DNA, these methods are incorporated by reference [27, 28].

The term "NK cells" as used herein refers to CD3-negative/CD56-positive mononuclear cells, and have a cytotoxic activity against cells in which expression of MHC class I molecules is reduced or the expression is lost.

The term "hematopoietic precursor cells" as used herein includes any cells having differentiation potency into blood cells of any one of cell types. The hematopoietic precursor cells of the present invention include, but are not limited to, an umbilical cord blood, hematopoietic stem cells derived from an adult blood cell tissue such as a bone marrow, hematopoietic precursor cells differentiation induced from induced pluripotent stem cells, embryonic stem cells and/or adult stem cells, and hematopoietic precursor cells directly converted from differentiated cells of fibroblasts or the like. The hematopoietic precursor cells of the present invention are included in CD34-positive cells. The hematopoietic precursor cells of the present invention may be prepared, however, by a method using a marker other than CD34 as long as CD34-positive cells are substantially contained. The hematopoietic precursor cells of the present invention may be prepared by any procedures known to those skilled in the art. For example, in collecting mononuclear cells from an umbilical cord blood, specific gravity centrifugation may be employed. Besides, hematopoietic precursor cells present in an umbilical cord blood can be selectively collected from mononuclear cells derived from the umbilical cord blood by using immunomagnetic beads on which an antibody to a cell surface marker is immobilized. As the immunomagnetic beads, Dynabeads (registered trademark) manufactured by Dynal and available from Invitrogen, or CliniMACS (registered trademark) manufactured by Miltenyi Biotec may be used, but the immunomagnetic beads are not limited to these. On the immunomagnetic beads, an anti-CD34 antibody is preferably immobilized. However, immunomagnetic beads on which another specifically bonding partner such as an antibody to a cell surface marker different from CD34 is immobilized may be used as long as CD34-positive cells derived from the umbilical cord blood can be collected. Besides, the hematopoietic precursor cells can be isolated/identified by performing immunofluorescent staining with a specific antibody to a cell surface marker and by using a flow cytometer. In the expansion method of the present invention, mononuclear cells separated from an umbilical cord blood may be cryopreserved and thawed in accordance with a time of transplantation to a patient to be used for expanding NK cells in some cases. The cryopreservation and thaw of the cells may be performed any method known to those skilled in the art. For the cryopreservation of the cells, any of commercially available cell cryopreservation solutions is used in some cases.

If the hematopoietic precursor cells are differentiation induced from induced pluripotent stem cells, embryonic stem cells and/or adult stem cells, the hematopoietic precursor cells may be differentiation induced from undifferentiated pluripotent stem cells by employing a culturing condition not using feeder cells and a serum, such as one reported by Niwa, A. et al., (PLoS ONE 6(7): e22261 (2011)), in some cases. To be brief, human ES cells or human iPS cells are allowed to form colonies in a serum-free medium for retaining the cells in an undifferentiated state, the medium is replaced with a serum-free medium for differentiation induction supplemented with BMP4, and with this day set as day 0, the cells are cultured up to day 4. On day 4, the medium is replaced with a serum-free medium for differentiation induction supplemented with VEGF and SCF instead of BMP4, and the cells are cultured up to day 6. Thereafter, on day 6, the medium is replaced with a serum-free medium for differentiation induction supplemented with a stem cell factor (SCF), thrombopoietin (TPO), interleukin 3 (IL-3), FMS-like tyrosine kinase 3 ligand (Flt3L), a fusion protein of IL-6 receptor and IL-6 (FP6), and the like. On day 10 to 12, a cluster of hematopoietic cells starts to be observed in a margin of the colony, and starts to float in the medium several days later.

If the hematopoietic precursor cells are directly converted from differentiated cells such as fibroblasts, for example, a method reported by Szabo, E. et al. (Nature, 468: 521 (2010)) may be employed in some cases. To be brief, OCT4 protein is forcedly expressed in differentiated cells such as human fibroblasts, and cultured in a medium supplemented with a basic fibroblast growth factor (bFGF), insulin-like growth factor II (IGF-II), Flt-3L and SCF. After about 21 days, CD45-positive cells appear. The CD45-positive cells are transferred to another culture vessel, and are further cultured in a medium for hematopoietic differentiation supplemented with SCF, G-CSF, Flt-3L, IL-3, IL-6 and BMP-4. About a quarter of the CD45-positive cells obtained about 16 days after the cultivation in the medium for hematopoietic differentiation are positive also to CD34. Such cells are further differentiation induced into any of various blood cell types.

The term "umbilical cord blood" as used herein refers to both a fresh umbilical cord blood collected from an umbilical cord at the time of delivery and an umbilical cord blood in a frozen state available through an umbilical cord blood bank system in which an umbilical cord blood is cryopreserved after obtaining test data for histocompatibility.

"Binding" refers to a sequence-specific, non-covalent interaction between macromolecules. Not all components of a binding interaction need be sequence-specific (e.g., contacts with phosphate residues in a DNA backbone), as long as the interaction as a whole is sequence-specific.

"binding protein" is a protein that is able to bind to another molecule. A binding protein can bind to, for example, a DNA molecule (a DNA-binding protein), an RNA molecule (an RNA-binding protein) and/or a protein molecule (a protein-binding protein).

"CRISPR/Cas nuclease" or "CRISPR/Cas nuclease system" includes a non-coding RNA molecule (guide) RNA that binds to DNA and Cas proteins (Cas9) with nuclease functionality (e.g., two nuclease domains). See, e.g., U.S. Provisional Application No. 61/823,689. Collectively, CRISPR system refers to transcripts and other elements involved in the expression of or directing the activity of CRISPR-associated ("Cas") genes, including sequences encoding a Cas gene, a tracr (trans-activating CRISPR), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. A sequence or template that may be used for recombination into the targeted locus comprising the target sequences is referred to as an "editing template" or "editing polynucleotide" or "editing sequence". In aspects of the invention, an exogenous template polynucleotide may be referred to as an editing template. In an aspect of the invention the recombination is homologous recombination.

"Cleavage" within the context of the current invention refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

"guide sequence" is any polynucleotide sequence having sufficient complementarity with a target polynucleotide sequence to hybridize with the target sequence and direct sequence-specific binding of a CRISPR complex to the target sequence.

"sequence" refers to a nucleotide sequence of any length, which can be DNA or RNA; can be linear, circular or branched and can be either single-stranded or double stranded. The term "donor sequence" refers to a nucleotide sequence that is inserted into a genome.

"target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

"Checkpoint genes" are genes or protein products thereof that inhibit immune responses. Within the context of the invention, checkpoint genes include: a) the E3 ubiquitin ligase Cbl-b; b) CTLA-4; c) PD-1; d) TIM-3; e) killer inhibitory receptor (KIR); f) LAG-3; g) CD73; h) Fas; i) the aryl hydrocarbon receptor; j) Smad2; k) Smad4; l) TGF-beta receptor; and m) ILT-3.

"Nucleic acid," "polynucleotide," and "oligonucleotide refers to a deoxyribonucleotide or ribonucleotide polymer, in linear or circular conformation, and in either single- or double-stranded form. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

As used herein, the term "RNA interference inducing molecule" or "RNAi molecule" or "RNAi agent" are used interchangeably herein to refer to an RNA molecule, such as a double stranded RNA, which functions to inhibit gene expression of a target gene through RNA-mediated target transcript cleavage or RNA interference. Stated another way, the RNA interference inducing molecule induces gene silencing of the target gene. The overall effect of an RNA interference inducing molecule is gene silencing of the target gene. A double-stranded RNA, such as that used in siRNA, has different properties than single-stranded RNA, double-stranded DNA or single-stranded DNA. Each of the species of nucleic acids is bound by mostly non-overlapping sets of binding proteins in the cell and degraded by mostly non-overlapping sets of nucleases. The nuclear genome of all cells is DNA-based and as such is unlikely to produce immune responses except in autoimmune disease (Pisetsky. Clin Diagn Lab Immunol. 1998 January; 51:1-6). Single-stranded RNA (ssRNA) is the form endogenously found in eukaryotic cells as the product of DNA transcription. Cellular ssRNA molecules include messenger RNAs (and the progenitor pre-messenger RNAs), small nuclear RNAs, small nucleolar RNAs, transfer RNAs and ribosomal RNAs. Single-stranded RNA can induce interferon and inflammatory immune response via TLR7 and TLR8 receptors (Proc Natl Acad. Sci. 2004. 101:5598-603; Science. 2004. 303: 1526-9; Science. 2004. 303:1529-3). Double-stranded RNA induces a size-dependent immune response such that dsRNA larger than 30 bp activates the interferon response, while shorter dsRNAs feed into the cell's endogenous RNA interference machinery downstream of the Dicer enzyme. MicroRNAs (miRNAs), including short temporal RNAs and small modulatory RNAs, are the only known cellular dsRNA molecules in mammals and were not discovered until 2001 (Kim. 2005. Mol. Cells. 19:1-15). Response to extracellular RNA in the bloodstream, double- or single-stranded of any length, is rapid excretion by the kidneys and degradation by enzymes (PLOS Biol. 2004. 2:18-20). As used herein, the term "effects RNA interference" refers to the initiation or causation of RNAi-mediated gene silencing, or to conditions that result in RNA interference-mediated gene silencing.

It is also known that the RNA interference does not have to match perfectly to its target sequence. Preferably, however, the 5' and middle part of the antisense (guide) strand of the siRNA is perfectly complementary to the target nucleic acid sequence. The RNA interference-inducing molecule according to the present invention includes RNA molecules that have natural or modified nucleotides, natural ribose sugars or modified sugars and natural or modified phosphate backbone. Accordingly, the RNA interference-inducing molecule referred to in the specification includes, but is not limited to, unmodified and modified double stranded (ds) RNA molecules including, short-temporal RNA (stRNA), small interfering RNA (siRNA), short-hairpin RNA (shRNA), microRNA (miRNA), double-stranded RNA (dsRNA), (see, e.g. Baulcombe, Science 297:2002-2003, 2002). The dsRNA molecules, e.g. siRNA, also may contain 3' overhangs, preferably 3'UU or 3'TT overhangs. In one embodiment, the siRNA molecules of the present invention do not include RNA molecules that comprise ssRNA greater than about 30-40 bases, about 40-50 bases, about 50 bases or more. In one embodiment, the siRNA molecules of the present invention have a double stranded structure. In one embodiment, the siRNA molecules of the present invention are double stranded for more than about 25%, more than about 50%, more than about 60%, more than about 70%, more than about 80%, more than about 90% of their length.

As used herein, "gene silencing" induced by RNA interference refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without introduction of RNA interference. In one preferred embodiment, the mRNA levels are decreased by at least about 70%, about 80%, about 90%, about 95%, about 99%, about 100%.

The term "reduced" or "reduce" as used herein generally means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease, or any integer decrease between 10-100% as compared to a reference level.

The term "increased" or "increase" as used herein generally means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any integer increase between 10-100% as compared to a reference level, or about a 2-fold, or about a 3-fold, or about a 4-fold, or about a 5-fold or about a 10-fold increase, or any increase between 2-fold and 10-fold or greater as compared to a reference level.

The RNA interference as described to inhibit NR2F6 also includes RNA molecules having one or more non-natural nucleotides, i.e. nucleotides other than adenine "A", guanine "G", uracil "U", or cytosine "C", a modified nucleotide residue or a derivative or analog of a natural nucleotide are also useful. Any modified residue, derivative or analog may be used to the extent that it does not eliminate or substantially reduce (by at least 50%) RNAi activity of the dsRNA. These forms thus include, but are not limited to, aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NH.sub.2 UTP, 2'NH.sub.2 CTP, and 2'F UTP. Such modified nucleotides include, but are not limited to, aminoallyl uridine, pseudo-uridine, 5-I-uridine, 5-I-cytidine, 5-Br-uridine, alpha-S adenosine, alpha-S cytidine, alpha-S guanosine, alpha-S uridine, 4-thio uridine, 2-thio-cytidine, 2'NH.sub.2 uridine, 2'NH.sub.2 cytidine, and 2' F uridine, including the free pho (NTP) RNA molecules as well as all other useful forms of the nucleotides. The RNA interference as referred herein additionally includes RNA molecules which contain modifications in the ribose sugars, as well as modifications in the "phosphate backbone" of the nucleotide chain. For example, siRNA or miRNA molecules containing .alpha.-D-arabinofuranosyl structures in place of the naturally-occurring .alpha.-D-ribonucleosides found in RNA can be used in RNA interference according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotides molecules similar to the oligonucleotides containing 2'-O-methyl ribose, arabinose and particularly .alpha.-arabinose (U.S. Pat. No. 5,177,196 which is incorporated herein in its entirety by reference). Also, phosphorothioate linkages can be used to stabilize the siRNA and miRNA molecules (U.S. Pat. No. 5,177,196). siRNA and miRNA molecules having various "tails" covalently attached to either their 3'- or to their 5'-ends, or to both, are also been known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Various specific siRNA and miRNA molecules have been described and additional molecules can be easily designed by one skilled in the art. For example, the miRNA Database at world-wide-web address: sanger.ac.uk, followed by /Software/Rfam/mirna/index provides a useful source to identify additional miRNAs useful according to the present invention (Griffiths-Jones S. NAR, 2004, 32, Database Issue, D109-D111; Ambros V, Bartel B, Bartel D P, Burge C B, Carrington J C, Chen X, Dreyfuss G, Eddy S R, Griffiths-Jones S, Marshall M, Matzke M, Ruvkun G, Tuschl T. RNA, 2003, 9(3), 277-279).

"expression vector" refers to a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); .beta.-lactamase, lac, ara, tet, trp, 1P.sub.L, 1P.sub.R, T7, tac, and trc promoters (useful for expression in *Escherichia coli*); light regulated-, seed specific-, pollen specific-, ovary specific-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art including, but are not limited to, the SV40 early (SV40e) promoter region, the promoter contained in the 3' long terminal repeat (LTR) of Rous sarcoma virus (RSV), the promoters of the EIA or major late promoter (MLP) genes of adenoviruses (Ad), the cytomegalovirus (CMV) early promoter, the herpes simplex virus (HSV) thymidine kinase (TK) promoter, a baculovirus 1E1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, .alpha.-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell .alpha.-actin, and the like. In addition, these expression sequences may be modified by addition of enhancer or regulatory sequences and the like.

An "siRNA" as used herein relates to a nucleic acid that forms a double stranded RNA, which double stranded RNA has the ability to reduce or inhibit expression of a gene or target gene when the siRNA is expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

siRNAs also include small hairpin (also called stem loop) RNAs (shRNAs). In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand may precede the nucleotide loop structure and the antisense strand may follow.

In another embodiment, siRNAs useful according the methods of the present invention are found in WO 05/042719, WO 05/013886, WO 04/039957, and U.S. Pat. App. No. 20040248296 which are incorporated in their entirety herein by reference. Other useful siRNAs useful in the methods of the present invention include, but are not limited to, those found in U.S. Pat. App. Nos. 20050176666, 20050176665, 20050176664, 20050176663, 20050176025, 20050176024, 20050171040, 20050171039, 20050164970, 20050164968, 20050164967, 20050164966, 20050164224, 20050159382, 20050159381, 20050159380, 20050159379, 20050159378, 20050159376, 20050158735, 20050153916, 20050153915, 20050153914, 20050148530, 20050143333, 20050137155, 20050137153, 20050137151, 20050136436, 20050130181, 20050124569, 20050124568, 20050124567, 20050124566, 20050119212, 20050106726, 20050096284, 20050080031, 20050079610, 20050075306, 20050075304, 20050070497, 20050054598, 20050054596, 20050053583, 20050048529, 20040248174, 20050043266, 20050043257, 20050042646, 20040242518, 20040241854, 20040235775, 20040220129, 20040220128, 20040219671, 20040209832, 20040209831, 20040198682, 20040191905, 20040180357, 20040152651, 20040138163, 20040121353, 20040102389, 20040077574, 20040019001, 20040018176, 20040009946, 20040006035, 20030206887, 20030190635, 20030175950, 20030170891, 20030148507, 20030143732, and WO 05/060721, WO 05/060721, WO 05/045039, WO 05/059134, WO 05/045041, WO 05/045040, WO 05/045039, WO 05/027980, WO 05/014837, WO 05/002594, WO 04/085645, WO 04/078181, WO 04/076623, and WO 04/04635, which are all incorporated herein in their entirety by reference.

The RNA interference according to the present invention can be produced using any known techniques such as direct chemical synthesis, through processing of longer double stranded RNAs by exposure to recombinant Dicer protein or *Drosophila* embryo lysates, through an in vitro system derived from S2 cells, using phage RNA polymerase, RNA-dependant RNA polymerase, and DNA based vectors. Use of cell lysates or in vitro processing may further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

The RNA interference, useful in the methods of the present invention include siRNAs that target gene expression of any protein encoded inside a eukaryotic cell. Examples of these proteins include endogenous mammalian proteins, parasitic proteins, viral proteins encoded by an eukaryotic cell after entry of a virus into the cell. Examples of methods of preparing such RNA interference are shown, for example in an international patent application Nos. PCT/US03/34424, PCT/US03/34686, and U.S. provisional patent applications Nos. 60/488,501, 60/488,155 and 60/516,172 the contents and references of all of these patent applications are herein incorporated by reference in their entirety.

Unlike the siRNA delivery methods described in the prior art, the method of the present invention allows targeting of specific cells to minimize or to avoid completely undesired potential side effects of siRNA therapy.

The invention provides means of generating tumor cytotoxic lymphoid cells such as natural killer (NK) cells. NK cells do not attack normal cells expressing MHC class I molecules but mainly attack cells in which the expression of the MHC class I molecules is reduced or lost. Since the expression of the MHC class I molecules is reduced in cancer cells or cells infected with a virus, NK cells can attack these cells. Therefore, if allogeneic NK cells are used in cell therapy of a cancer or an infectious disease, it is advantageous that there is no need to precedently immunize the NK cells for causing them to recognize target cells, and that an adverse reaction of GVH (Graft-versus-host) disease can be avoided. When a cancer patient was a recipient and concentrated NK cells obtained from fresh peripheral blood mononuclear cells of a healthy donor closely related to the recipient were transplanted, the transplanted NK cells temporarily survived without causing an adverse reaction in the recipient and retained their cytotoxic activity. There is, however, no report on a clinical trial showing the effectiveness of NK cell transplantation therapy. One of the reasons is that the number of cells collectable from a donor by lymphocyte apheresis is limited, and hence, NK cells in number sufficient for killing target cells, such as cancer cells or cells infected with a pathogen, cannot be caused to stay in the body of a recipient until the target cells are killed. 2, a survival period of NK cells is not correlated with the number of administered NK cells, but is merely 2 to 189 days, with a median as small as 10 days. Therefore, in order to cause NK cells in number sufficient for killing target cells, such as cancer cells or cells infected with a pathogen, to stay in the body of a recipient until the target cells are killed, it is necessary to frequently repeat the NK cell transplantation, which is a great burden of the patient. Accordingly, a technique in which NK cells obtained from a donor are once cultured in a test tube to obtain NK cells in number sufficient for killing target cells has been developed. In this technique, use of a serum or feeder cells of an animal is not preferred because a risk of infection is otherwise caused in prepared NK cells.

Umbilical cord bloods of various blood types are classified and stored in an umbilical cord blood bank, and thus if an umbilical cord blood is used as an origin of NK cells for use in a treatment, it is easy to select, based on the blood type of a patient, an umbilical cord blood of a blood type that has high histocompatibility and low possibility of an adverse reaction caused by the transplantation. Therefore, a technique in which NK cells for use in a treatment are prepared from an umbilical cord blood without using a serum or feeder cells of an animal has recently attract attention. It is reported that NK cells were prepared in number ten thousand times or more in 6 weeks from CD34-positive cells derived from a cryopreserved umbilical cord blood. It cannot be said, however, that the cytotoxic activity of the NK cells obtained by the method of this report is high. Besides, in the conventional technique, for the preparation of NK cells from hematopoietic precursor cells, it is necessary to replace, during the preparation, a medium with one having a different cytokine composition. The invention teaches means of overcoming these deficiencies by either gene silencing or gene editing checkpoint inhibitors on cord blood derived cells that are programmed in vitro to become cytotoxic to tumor cells.

Cord blood is a unique source of starting material for the practice of the invention. Citations are incorporated by reference to allow one of skill in the art to practice the invention, for example, publications describe the use of cord blood in oncology as a substitute for bone marrow [16-21]. Outside the area of oncology, the clinical use of cord blood has expanded into various areas that range from reconstituting a defective immune system [22], to correcting congenital hematological abnormalities [23], to inducing angiogenesis [24]. Cord blood is known to contain a variety of cellular types. For the practice of the invention it is important to initiate cultures with cells of lymphoid origin, such as NK cells, T cells, or progenitors thereof. In some embodiments, other cells in cord blood may be utilized in order to allow for increased proliferation of T cells in cord blood. In other embodiments, T cells are generated form the cord blood stem cells in vitro. The original clinically attractive feature of cord blood was the high concentration of hematopoietic stem cells, which is similar to that found in bone marrow: approximately 0.1-0.8 $CD34^+$ cells per 100 nucleated cells. However, in contrast to marrow, $CD34^+$ cells from cord blood possess higher proliferative potential in vitro [29], superior numbers of long term culture initiating cells and SCID repopulating cells [30, 31], as well as higher telomerase activity [32]. The potent hematopoietic activity of cord blood derived $CD34^+$ cells may be attributed to the fact that cord blood is a much more developmentally immature source of stem cells as opposed to stem cells derived from adult sources. Attesting to the robust hematopoietic activity of cord blood derived $CD34^+$ cells in comparison to bone marrow cells is the fact that successful reconstitution, albeit delayed, of post-ablative hematopoiesis occurs in patients receiving approximately one tenth of the total nucleated cell number in a cord blood graft compared to a bone marrow graft. The use of cord blood derived hematopoietic stem cells to generate T cells or NK cells in vitro has previously been described and is part of the current invention, subsequent or prior to gene silencing and/gene editing for inhibition/deletion of a checkpoint. In addition to being a source of hematopoietic cells, cord blood contains potent angiogenesis stimulating cells. Several phenotypes have been ascribed to cord blood angiogenic stimulating cells. In one report, the $CD34^+$, $CD11b^+$ fraction, which is numerically approximately less than half of the $CD34^+$ fraction of cord blood was demonstrated to possess ability to differentiate into functional endothelial cells in vitro and in vivo [33]. In another report, $VEGF-R3^+$, $CD34^+$ cells were shown to possess not only the ability to differentiate into endothelial cells in vivo, but also to be able to expand on a per cell number by approximately 40-fold in vitro and still maintain function when transferred in vivo. The same study demonstrated that the concentration of this endothelial progenitor fraction found in cord blood $CD34^+$ cells is approximately tenfold higher as compared to bone marrow $CD34^+$ cells [34]. Regardless of the phenotype of the cord blood cell with angiogenesis stimulating ability, unfractionated cord blood mononuclear cells have also been used in numerous animal models [35-37], as well as in the clinic [24], for successful stimulation of angiogenesis. One particularly interesting characteristic of cord blood endothelial progenitors is that they respond by proliferating and stimulating angiogenesis to agents, which normally would inhibit angiogenesis of bone marrow progenitors [37]. In one aspect of the invention these endothelial cells may be transfected with T cell and/or NK cell stimulatory molecules in order to allow for more effective expansion of cord blood lymphoid cells. In addition to endothelial progenitors, mesenchymal stem cells (discussed below in more detail), which are found in cord blood, are known to secrete numerous cytokines and growth factors such as VEGF and FGF-2 [38, 39] which stimulate angiogenic processes. In fact, there are reports of mesenchymal stem cells contributing to angiogenesis through direct differentiation into endothelial cells [40]. Mesenchymal stem cells are a type of cell capable of differentiating into various non-hematopoietic tissues. Currently this cell population is second to bone marrow stem cells in terms of clinical entry in that Phase III clinical trials are already underway with these cells. Mesenchymal stem cells are classically defined as adhere to plastic and expressing a non-hematopoietic cell surface phenotype, consisting of $CD34^-$, $CD45^-$, $HLA-DR^-$, while possessing markers such as STRO-1, VCAM, CD13, CD29, CD44, CD90, CD105, SH-3, and STRO-1 [41]. To date mesenchymal stem cells have been purified from bone marrow [42], adipose tissue [43], placenta [44, 45], scalp tissue [46] and cord blood [47]. Cord blood-derived mesenchymal stem cells have demonstrated ability to differentiate into a wide variety of tissues in vitro including neuronal [48-50], hepatic [51, 52], osteoblastic [53], and cardiac [47]. An important aspect of this cell population is their anti-inflammatory and immunomodulator activity. For example, they constitutively secrete immune inhibitory cytokines such as IL-10 and TGF-□ while maintaining ability to present antigens to T cells, thus suggesting they may act as a tolerogenic antigen presenting cell [54, 55]. Conceptually, the mesenchymal content of umbilical cord blood grafts may explain the tolerogenic capabilities, which some have speculated to be donor specific. Although the majority of published studies have examined bone marrow derived mesenchymal stem cells, and thus are outside the scope of the present review, it is important to note differences between mesenchymal stem cells derived from different sources. A recent study compared mesenchymal stem cells from bone marrow, cord blood and adipose. Cord blood mesenchymal stem cells which were capable of expansion to approximately 20 times, whereas adipose derived cells expanded an average of 8 times and bone marrow derived cells expanded 5 times [56]. This, and other studies support the important role of mesenchymal stem cell content in the biological activities of the cord blood graft. The mesenchymal stem cell component of cord blood may inhibit T cell activation, according these cells need to be themselves either gene silencing/gene edited, or modified to reduce expression of immune suppressive cytokines but enhance expression of immune stimulatory cytokines. Another possibility is removing these cells from culture. Cells with markers and activities resembling embryonic stem cells have been found in cord blood. Zhao et al identified a population of $CD34^-$ cells expressing OCT-4, Nanog, SSEA-3 and SSEA-4, which could differentiate into cells of the mesoderm, ectoderm and endoderm lineage. In vivo administration of these cells into the streptozotocin-induced murine model of diabetes was able to significantly reduce hypoglycemia [57]. The existence of cells with such pluripotency in cord blood was also observed by Kogler et al who identified an Unrestricted Somatic Stem Cell (USSC) with capability of differentiation into functional osteoblasts, chondroblasts, adipocytes, hematopoietic and neural cells. USSC were demonstrated to be capable of >40 population doublings in vitro without spontaneous differentiation or loss of telomere length. Interestingly, administration of these cells (derived from human cord blood) into fetal sheep resulted significant human hematopoiesis (up to 5%), hepatic chimerism with >20% albumin-producing human parenchymal hepatic cells, as well as detection of human cardiomyocytes. The mechanism of differentiation was not associated with fusion [58]. Support for presence of such pluripotency in cord blood cells also comes from a similar experiment in which CD34$^+$ Lineage$^-$ cells were transfected with GFP and administered in utero to goats. GFP cells were detected in blood, bone marrow, spleen, liver, kidney, muscle, lung, and heart of the recipient goats (1.2-36% of all cells examined) [59].

When cord blood is directly expanded for T cells or NK cells for the practice of the invention, attention needs to be paid to other cells in cord blood that modulate allogenicity. It is not accurate to simply state that cord blood contains the same percentages of cells as found in adult blood but at a more immature and non-immunogeneic state: cord blood cells possess dominant and passive tolerogeneic mechanisms, in part for protecting the infant from excess inflammatory stimuli which would have disastrous consequences on developmental processes. Given the above description of some of the subpopulations of stem cells found in cord blood, we now will describe some of the immunological characteristics of these cells.

The most potent antigen presenting cell of the immune system, the dendritic cell, possesses unique properties when it is isolated from cord blood. While circulating dendritic cells from adult blood are potent stimulators of the mixed lymphocyte reaction (MLR), and co-stimulators of mitogen induced T cell proliferation, dendritic cells derived from cord blood are poor, or even inhibitory, to both measures of immune functions [60, 61] [62]. One possible explanation may be that cord blood dendritic cells possess a predominantly lymphoid phenotype and have lower expression of costimulatory molecules as opposed to adult blood-derived dendritic cells [63-66].

Mechanistically, several studies have shown that cord blood dendritic cells are involved in the anti-inflammatory Th2 bias of the neonate [63-65]. Unique properties of immune suppression, or deviation are observed in that cord blood dendritic cell progenitors exhibit enhanced susceptibility both natural and artificial immune suppressants [67]. In support of such non-immune activating properties, when cord blood versus peripheral blood derived dendritic cells are assessed for ability to stimulate immune response to apoptotic or necrotic cells, peripheral blood derived dendritic cells upregulate costimulatory molecules and stimulate T cell proliferation, whereas cord blood derived dendritic cells do not [68]. Given the above-mentioned properties of cord blood cells it conceptually is possible that these cells have an increased predisposition towards tolerogenicity. An example of this is that growth of cord blood progenitors, but not adult, in M-CSF gives rise to a cell population that exhibits potently suppressive tolerogenic dendritic cell phenotype. These cells are not only are poor allostimulators, but are able to expand CD4$^+$ CD25$^+$ T regulatory cells that are capable of inhibiting mixed lymphocyte reactions [69]. Another interesting tolerogenic feature of cord blood dendritic cells is their propensity to secrete large numbers of MHC II-bearing exosomes that lack expression of costimulatory molecules [70]. This type of exosome was used for prevention of autoimmune disease by other authors [71]. Given the immaturity and anti-inflammatory activity of cord blood dendritic cells, it is suggested that cord blood in general will be more poorly immunogenic as compared to other sources of nucleated cells. A comparison may be made between cord blood grafts and liver transplants in that HLA-matching for liver transplants does not seem to effect graft survival [72]. Indeed dendritic cell populations with a primarily lymphoid phenotype, similar to those found in cord blood are known to predominate in the liver [72]. Tissue transplantation across allogeneic barriers is limited by recipient recognition of antigen presenting cells in the graft, especially of dendritic cells, and subsequent launching of immune mediated rejection. Studies in which donor dendritic cell content is depleted or inactivated has allowed for increased survival of allografts, and even induction of tolerance. Given that the dendritic cells in cord blood are not immunogeneic, and actually possess features of tolerogeneicity, it may be possible that transplantation of cord blood into an allogeneic recipient will not result in immunologically mediated clearing of the graft. Experimental studies in this area are scarce, but it may also be worthwhile suggesting that due to the propensity for tolerance, the cord blood graft may easily be manipulated with various immune modulating agents to enhance its tolerogeneicity.

Cord blood has approximately similar concentrations of CD34$^+$ cells compared to bone marrow on a percentage of nucleated cell basis, however, these cells are significantly more active in terms of stimulating hematopoiesis as previously discussed. Here we will discuss some of the tolerogenic properties of bone marrow CD34$^+$ cells as may be of relevance to those found in cord blood. On the one hand, it is known that hematopoietic progenitor cells are inherently weak immunogens, as witnessed by their poor stimulatory activity of MLR. On the other hand, early studies suggested that CD34$^+$ hematopoietic cells are actually dominantly immune suppressive, in part through elaborating soluble immune inhibitor factors, including, but not limited to TGF-b. There are even publications stating that CD34$^+$ cells possess a "natural suppressor" phenotype and contribute to tumor growth through inhibition of anti-tumor immunity. In accordance with the notion that CD34$^+$ cells may be tolerogenic, are the observations that these cells actually have the ability to functionally inactivate immune cells that recognize them. This "veto effect" has been previously suggested as one of the reasons why high dose bone marrow transplants are associated with enhanced engraftment [73, 74]. Supporting this concept are studies in which induction of clinical transplantation tolerance using donor specific bone marrow has been demonstrated [75]. Mechanistically, in a murine model it was shown that the veto-like effect of donor bone marrow transplantation is dependent on expression of FasL on bone marrow cells [76]. Furthermore, human mixed lymphocyte reaction responder cells can be specifically induced to undergo apoptosis by stimulator, but not third party CD34$^+$ cells obtained from bone marrow [77]. It is at present uncertain if cord blood CD34$^+$ cells also possess similar veto activity. However, given that one of the reasons for the veto effect is the hypothesis that the hematopoietic compartment needs to protect itself from immune mediated inflammation, and given that cord blood CD34$^+$ cells are more potent hematopoietically than bone marrow CD34$^+$ cells, it would be natural that the cord blood cells would also have higher veto activity as opposed to bone marrow.

Mesenchymal stem cells with proliferative ability greater than bone marrow or adipose tissue are found in cord blood [78]. It is likely that this cell population plays an important role in the immunogenicity of the cord blood graft, both during the immediate transplantation period, and also in the long term when these cells engraft into donor tissue. Mesenchymal stem cells have been shown to possess immune suppressive functions. For example, it was demonstrated in a murine model that flk-1+ Sca-1-marrow derived mesenchymal stem cell transplantation leads to permanent donor-specific immunotolerance in allogeneic hosts and results in long-term allogeneic skin graft acceptance [79]. Other studies have shown that mesenchymal stem cells are inherently immunosuppressive through production of PGE-2, interleukin-10 and expression of the tryptophan catabolizing enzyme indoleamine 2,3,-dioxygenase as well as galectin-1 [80, 81]. These stem cells also have the ability to non-specifically modulate the immune response through the suppression of dendritic cell maturation and antigen presenting abilities [82, 83]. Immune suppressive activity is not dependent on prolonged culture of mesenchymal stem cells since functional induction of allogeneic T cell apoptosis was also demonstrated using freshly isolated, irradiated, mesenchymal stem cells [84]. In one aspect of the invention IDO is silenced in cord blood dendritic cells as a means of augmenting immunogenicity of the cord blood graft, or lymphoid killer cells generated in the cord blood graft.

It was demonstrated that mesenchymal stem cells have the ability to preferentially induce expansion of antigen specific T regulatory cells with the CD4+ CD25+ phenotype [85]. This would allow a localized injection of mesenchymal stem cells to initiate a self-maintaining tolerogenic activity that would remain even if the mesenchymal stem cells were removed. Antigen-specific immune modulation by mesenchymal stem cells was demonstrated in numerous models. For example, in the murine model of multiple sclerosis, experimental autoimmune encephalomyelitis, administration of these cells lead to inhibition of disease onset and in some animals complete protection [86]. An important caveat is the actual numbers and immune suppressive activity of mesenchymal stem cells in fresh cord blood as opposed to ex vivo expanded. This is an area that is currently under investigated. However, the possibility that mesenchymal stem cells preferentially expand in vivo from a small number of cells that are originally seeded should be taken into consideration. In fact, in the allogeneic setting of fetal to maternal trafficking, which will be discussed in detail later, mesenchymal-like cells are found in all mothers tested years after pregnancy [87].

The possibility of using cord blood in absence of host preconditioning would open up the door for a multitude of stem cell therapeutic applications. The currently dogma amongst cord blood transplanters is that administration of allogeneic cord blood, even if HLA-matched, would in the best case scenario lead to immunologically-mediated rejection or the graft, and in the worst case cause GVHD. Here we provide rationale for the preliminary clinical exploration of cord blood administration in a non-preconditioned host. In the 1930s it was reported that cord blood could be safely used as a substitute for peripheral blood for performing transfusions [88]. Since HLA-matching was not available at that time and no adverse effects were noted, feasibility of cord blood administration to a non-preconditioned host was suggested. A more recent Lancet publication described the use of cord blood as a source of blood donation for malaria infested regions in Africa. 128 pediatric patients with severe anemia needing transfusions were transplanted with an average of 85 ml of ABO matched cord blood with no HLA matching. No report of graft versus host was noted, and cord blood was proposed as a transfusion source when peripheral blood is not available due to economical or social reasons [89]. An extensive review of 129 patients transplanted with a total of 413 Units of cord blood (average 86 ml) with no preconditioning or HLA matching between 1999 to 2004 was published by Bhattacharya [90]. Of these patients, aged 2-86 years old and suffering from advanced cancer (56.58%) and other diseases (43.42%) such as ankylosing spondylitis, lupus erythematosus, rheumatoid arthritis, aplastic anemia, and thalassemia major, no immunological reactions were noted with followed for some patients of 1-4 years. The same author reported several other patient cohorts that have been similarly treated and had no GVHD or other immune reactions [91-94]. Furthermore, transfusion of cord blood in non-HLA matched recipients was also associated with transient increases in peripheral CD34 counts, without evidence of GVHD in patients with cancer and HIV [95, 96]. Unfortunately in these studies did not perform long-term molecular analysis for chimerism. Despite this drawback, it is evident from the initial work in the 1930s, to the numerous cases reported by Bhattacharya, to the publication in Lance, that administration of cord blood is a safe procedure not associated with immunological consequences. Thus based on the current data, the worse a cord blood transplant will do is do nothing.

The cells that are "dangerous" from the cord blood from a GVHD perspective are lymphocytes that may have alloreactive potential. Lymphocytes from cord blood, in contrast to adult blood, are generally immature and usually do not secrete as many inflammatory cytokines. Therefore administration of allogeneic lymphocytes purified from adult blood would be a much more dangerous procedure, at least as far as GVHD is concerned, in contrast to administration of lymphocytes from cord blood. The fact is administration of lymphocytes from paternal sources has been performed in numerous reports in the clinical practice of using "paternal lymphocyte immunotherapy" for treatment of spontaneous abortions. Numerous trials have been conducted administering doses of up to $2\times10^9$ paternal lymphocytes into pregnant mothers who have had recurrent miscarriages [97, 98]. These doses are higher than the $1.5$-$3\times10^7$ nucleated cells/kg administered during a cord blood transplant [99]. Interestingly, in pregnant women administered these high doses of completely allogeneic cells, no GVHD has ever been observed in mothers subjected to this procedure, although Th2 immune deviation has been reported by some groups [100, 101]. Thus according to the current evidence, there is no fear of GVHD being induced after cord blood transplant. Bhattacharya even administered as many as 32 units of cord blood without seeing GVHD [96].

The practitioner of the invention will ask, in response to the above arguments regarding GVHD-inducing ability of cord blood, "why is GVHD, a clinical reality in patients receiving cord blood for hematological malignancies?" The answer to this is that current day cord blood transplants take place following ablation of host T cells. This creation of an "empty compartment" allows for homeostatic expansion of the newly introduced T cells, which primes them for aggressive immune reactions and alleviates their requirement for costimulation [102]. It is known from the transplantation literature that T cells reconstituting a host that has been lymphoablated are resistant to costimulatory blockade and tolerance induction [103]. Furthermore the pioneering experiments of Rosenberg's group demonstrated that infusion of tumor specific lymphocytes following ablation of the recipient T cells, using conditions similar to those used in cord blood transplant preconditioning allows for highly aggressive anti-tumor responses that otherwise would not be observed [104]. Further supporting the concept that reconstitution of a lymphocyte deficient immune system can cause immune hyperreactivity comes from clinical observations of "autologous GVHD" in patients administered drugs associated with induction of lymphopenia [105, 106]. We therefore propose that GVHD is not an intrinsic property of the allogeneic cells introduced into the host, but a result of the lymphoablation induced in the recipient prior to cellular administration. If cord blood, or cytotoxic cells derived thereof can be administered into a non-preconditioned patient without fear of GVHD, then the next question arises as to whether the infused cells will actually endow some type of benefit or be rapidly cleared by the immune system. As previously mentioned, biological effects of mismatched cells, even if they are cleared by the immune system may have a beneficial role in inflammatory pathologies through exertion of a Th2 phenotype as seen in mothers being administered their mate's lymphocytes. Furthermore, even if transplanted cells are cleared by the immune system, it is known that apoptotic cells, can mediate various therapeutic anti-inflammatory effects that are clinically relevant [107]. non ablated. The inventors teach that complete immune mediated clearing of tumor killing cytotoxic lymphoid cord blood cells will not occurs in the allogeneic setting. One reason for this notion comes from an interesting phenomena observed in pregnancy. It is well established that during pregnancy fetal cells enter maternal circulation [108]. While circulating $CD34^+$ cells of fetal origin are found a percentage of women who have had children [109], in the bone marrow 100% of women who have had children were found to contain offspring-derived mesenchymal cells in their bone marrow [87]. Although some studies have correlated autoimmunity with residual lymphocytes causing a GVHD-like reaction in the mother, more careful analysis of these studies show that immune cells of fetal origin are largely outnumbered by cells of maternal origin. This is the basis for the proposition of Khosrotehrani et al that the fetal cells are actually "pregnancy associated progenitor cells" that act as allogeneic "repair cells" [110]. The authors of this hypothesis believe that these repair cells are actually migrating to the site of autoimmune damage in order to control injury and cause regeneration. The authors cite numerous examples in support of their idea, more notably, a case report of a hepatitis C patient who stopped treatment but disease relapse was not observed. Biopsy analysis demonstrated the liver parenchyma was heavily populated with cells of male origin that based on DNA polymorphism analysis were derived from a previous pregnancy more than a decade earlier [111]. Additionally, they cite reports of maternal cells differentiating into thyroid, cervix, gallbladder and intestinal epithelial cells [112-115]. Data from animal models, although scarce, supports the notion that fetal cells trafficking into the mother may play some reparative function. For example, it was reported that EGFP expressing fetal cells would selectively home into damaged maternal renal and hepatic tissues after gentamycin and ethanol induced injury [116]. Furthermore, another study demonstrated that subsequent to excitotoxic injury in the maternal brain, fetal-derived EFGP postive cells can be identified which express morphology and markers of neurons, astrocytes, and oligodendrocytes [117]. The authors of this paper are not stating that the fetal transfer of mesenchymal cells to the maternal host is an exact duplicate of an allogeneic cord blood transplant in absence of immune suppression. Rather, we are proposing fetal to maternal trafficking as a possible example of a natural biological situation in which stem cells may persist in an allogeneic environment without induction of complete tolerance.

The cord blood is utilized as a source of cytotoxic T cells and/or NK cells. In the NK cells obtained by the preparation method of the present invention, the pharmaceutical composition containing the NK cells and the cell therapy of the present invention, a solution for suspending or culturing living cells is, for example, a saline, a phosphate buffered saline (PBS), a medium, a serum or the like in general. The solution may contain a carrier pharmaceutically acceptable as a pharmaceutical or a quasi-pharmaceutical in some cases. The NK cells obtained by the preparation method of the present invention, the pharmaceutical composition containing the NK cells and the cell therapy of the present invention can be applied to treatment and/or prevention of various diseases having sensitivity to NK cells. Examples of such diseases include, but are not limited to, cancers and tumors such as an oral cancer, a gallbladder cancer, a cholangiocarcinoma, a lung cancer, a liver cancer, a colorectal cancer, a kidney cancer, a bladder cancer and leukemia, and infectious diseases caused by viruses, bacteria and the like. The pharmaceutical composition containing the NK cells of the present invention may contain, in addition to the NK cells prepared by the method of the present invention, an NK cell precursor, T cells, NKT cells, hematopoietic precursor cells and other cells in some cases. The cell therapy of the present invention may be practiced singly or in combination with surgical treatment, chemotherapy, radiation therapy or the like in some cases. In the cell therapy of the present invention, the NK cells expanded by the method of the present invention may be transplanted into a patient together with T cells and NKT cells in some cases. In the cell therapy of the present invention, the NK cells may be transplanted by, for example, intravenous, intraarterial, subcutaneous or intraperitoneal administration in some cases. In the method for preparing NK cells of the present invention, in the method for preparing the pharmaceutical composition of the present invention and in the cell therapy of the present invention, any of media such as, but not limited to, a KBM501 medium (Kohjin Bio Co., Ltd.), a CellGro SCGM medium (registered trademark, Cellgenix, Iwai Chemicals Company), a STEMLINE II (Sigma-Aldrich Co. LLC.), an X-VIVO15 medium (Lonza, Takara Bio Inc.), IMDM, MEM, DMEM and RPMI-1640 may be singly used as or blended in an appropriate ratio to be used as a medium for culturing cells in some cases. Besides, the media for culturing cells may be used with supplementation of at least one additional component selected from the group consisting of a serum, a serum albumin, an appropriate protein, a cytokine, an antibody, a compound and another component, which will be described below, in some cases.

The medium may be supplemented with an autologous serum of a subject, a human AB-type serum available from BioWhittaker Inc. or the like, or a donated human serum albumin available from Japanese Red Cross Society in some cases. The autologous serum and the human AB-type serum is supplemented preferably in a concentration of 1 to 10%, and the donated human serum albumin is supplemented preferably in a concentration of 1 to 10%. The subject may be a healthy person, or a patient having any of various diseases sensitive to NK cells. The medium may be supplemented with an appropriate protein, a cytokine, an antibody, a compound or another component as long as the effect of expanding NK cells is not impaired. The cytokine may be interleukin 2 (IL-2), interleukin 3 (IL-3), interleukin 7 (IL-7), interleukin 12 (IL-12), interleukin 15 (IL-15), interleukin 21 (IL-21), stem cell factor (SCF), thrombopoietin (TPO) and/or FMS-like tyrosine kinase 3 ligand (Flt3L) in some cases. The IL-2, IL-3, IL-7, IL-12, IL-15, IL-21, SCF, TPO and Flt3L preferably have a human amino acid sequence, and are preferably produced by a recombinant DNA technology from the safety viewpoint. The IL-15 is used preferably in a concentration of 0.1 to 100 ng/mL, more preferably in a concentration of 20 to 30 ng/mL, and particularly preferably in a concentration of 25 ng/mL. The SCF is used preferably in a concentration of 2 to 100 ng/mL, more preferably in a concentration of 20 to 30 ng/mL, and particularly preferably in a concentration of 25 ng/mL. The IL-7 is used preferably in a concentration of 0.5 to 100 ng/mL, more preferably in a concentration of 20 to 30 ng/mL, and particularly preferably in a concentration of 25 ng/mL. The Flt3L is used preferably in a concentration of 1 to 100 ng/mL, more preferably in a concentration of 20 to 30 ng/mL, and particularly preferably in a concentration of 25 ng/mL. The TPO is used preferably in a concentration of 1 to 100 ng/mL, more preferably in a concentration of 20 to 30 ng/mL, and particularly preferably in a concentration of 25 ng/mL. Herein, the concentration of the IL-2 may be shown in Japanese Reference Unit (JRU) and International Unit (IU). Since 1 IU corresponds to approximately 0.622 JRU, 1750 JRU/mL corresponds to approximately 2813 IU/mL. The IL-2 preferably has a human amino acid sequence and is preferably produced by a recombinant DNA technology from the safety viewpoint. The IL-2 is used preferably in a concentration of 100 to 2900 IU/mL, more preferably in a concentration of 100 to 2813 IU/mL, and particularly preferably 2813 IU/mL. In the preparation method of the present invention and in the cell therapy of the present invention, in the step of expanding hematopoietic precursor cells, the cells are cultured in a medium supplemented with IL-15, SCF, IL-7 and Flt3L. The medium may be supplemented further with TPO in some cases. The medium may be replaced at any time after starting the cultivation as long as a desired number of NK cells can be obtained, and is preferably replaced every 3 to 5 days. In the expansion of the hematopoietic precursor cells, the cell growth rate is abruptly lowered in about 5 weeks. Therefore, the expansion of the hematopoietic precursor cells is conducted for about 5 weeks, namely, for 32, 33, 34, 35, 36, 37 or 38 days, after starting the cultivation. Thereafter, from the expanded hematopoietic precursor cells, NK cells are differentiation induced. In the step of differentially inducing NK cells, the cells are cultured in a medium supplemented with IL-2. The differentiation induction of NK cells is conducted for about 1 week, namely, for 5, 6, 7, 8 or 9 days. Here, cultivation conducted for n days under a given culturing condition refers to that the cultivation is conducted from a cultivation start date to n days after under the culturing condition, and means that transition to a next culturing condition or cell collection is performed n days after starting the cultivation. In the present invention, the hematopoietic precursor cells may be frozen during the expansion or after completing the expansion, and thawed in accordance with a time of transplantation into a patient to be used for the transplantation into the patient in some cases. The cells may be frozen and thawed by any of methods known to those skilled in the art. For freezing the cells, any of commercially available cryopreservation solutions is used in some cases.

In the expansion method of the present invention, the culture vessel includes, but is not limited to, commercially available dishes, flasks, plates and multi-well plates. The culturing condition is not especially limited as long as the effect of expanding NK cells is not impaired, but a culturing condition of 37.degree. C., 5% CO.sub.2 and a saturated water vapor atmosphere is generally employed. Since the purpose of the present invention is to prepare a large amount of NK cells, it is advantageous that the time period of culturing the cells in the medium is longer because a larger amount of NK cells can be thus obtained. The culture period is not especially limited as long as the NK cells can be expanded to a desired number of cells.

The method and the production of the pharmaceutical composition of the present invention are practiced preferably under conditions complying with good manufacturing practices (GMP) for pharmaceuticals and quasi-pharmaceuticals. The cytotoxic activity of the NK cells thus prepared is evaluated by a method known to those skilled in the art. In general, the cytotoxic activity is quantitatively determined by incubating the NK cells (effector cells) and target cells labeled with a radioactive substance, a fluorescent dye or the like, and then measuring a radiation dose or a fluorescence intensity. The target cells may be K562 cells, acute myelogenous leukemia cells, or chronic myelogenous leukemia cells in some cases, but are not limited to these. The properties of the expanded NK cells may be checked by employing RT-PCR, solid phase hybridization, ELISA, Western blotting, immune precipitation, immunonephelometry, FACS, flow cytometry or the like in some cases. In the present invention, the collection and cryopreservation of an umbilical cord blood and/or adult blood cell tissue, the preparation of an autologous serum, the preparation of an umbilical cord blood and/or adult blood cell tissue, and mononuclear cells differentiation induced from pluripotent stem cells such as induced pluripotent stem cells, embryonic stem cells or adult stem cells, the preparation of hematopoietic precursor cells from the mononuclear cells, the measurement of the number of cells before and after the cultivation of the hematopoietic precursor cells, the measurement of a constituent ratio among NK cells, T cells and other cell types in the hematopoietic precursor cells before and after the cultivation, the calculation of the expansion factor of the NK cells, and the statistical analysis of a measurement error or significance may be practiced by any methods known to those skilled in the art.

The present invention provides cell therapy. The cell therapy of the present invention includes a step of expanding hematopoietic precursor cells under a single culturing condition; and a step of differentially inducing the cells obtained in the expanding step into NK cells. In the cell therapy, a medium used in the step of expanding hematopoietic precursor cells under a single culturing condition may be supplemented with IL-15, SCF, IL-7 and Flt3L in some cases. In the cell therapy, the medium used in the step of expanding hematopoietic precursor cells under a single culturing condition may be supplemented further with TPO in some cases. In the cell therapy, the step of differentially inducing the NK cells may include culturing the expanded hematopoietic precursor cells under a culturing condition containing IL-2 in some cases. In the cell therapy, the medium used in each of the steps may be supplemented with a human AB-type serum and/or a human serum albumin. In the cell therapy, the hematopoietic precursor cells may be at least one of hematopoietic precursor cells selected from the group consisting of hematopoietic precursor cells contained in an umbilical cord blood and/or an adult blood cell tissue, hematopoietic precursor cells differentiation induced from induced pluripotent stem cells, embryonic stem cells and/or adult stem cells, and hematopoietic precursor cells directly converted from differentiated cells. In the cell therapy, the step of transplanting the NK cells into a patient may be a step of transplanting the NK cells together with other cells such as T cells or NKT cells in some cases. The cell therapy of the present invention may be employed for treating and/or preventing an infectious disease and/or a cancer.

Production of NK cells by the present method comprises expanding a population of hematopoietic cells. During cell expansion, a plurality of hematopoietic cells within the hematopoietic cell population differentiate into NK cells. In one embodiment, provided herein is a method of producing a population of activated natural killer (NK) cells, comprising: (a) seeding a population of hematopoietic stem or progenitor cells in a first medium comprising interleukin-15 (IL-15) and, optionally, one or more of stem cell factor (SCF) and interleukin-7 (IL-7), wherein said IL-15 and optional SCF and IL-7 are not comprised within an undefined component of said medium, such that the population expands, and a plurality of hematopoietic stem or progenitor cells within said population of hematopoietic stem or progenitor cells differentiate into NK cells during said expanding; and (b) expanding the cells from step (a) in a second medium comprising interleukin-2 (IL-2), to produce a population of activated NK cells. In another embodiment, NK cells provided herein are produced by a two-step process of expansion/differentiation and maturation of NK cells. The first and second steps comprise culturing the cells in media with a unique combination of cellular factors. In certain embodiments, the process involves (a) culturing and expanding a population of hematopoietic cells in a first medium, wherein a plurality of hematopoietic stem or progenitor cells within the hematopoietic cell population differentiate into NK cells; and (b) expanding the NK cells from step (a) in a second medium, wherein the NK cells are further expanded and differentiated, and wherein the NK cells are maturated (e.g., activated or otherwise possessing cytotoxic activity). In certain embodiments, the method includes no intermediary steps between step (a) and (b), no additional culturing steps prior to step (a), and/or no additional steps (e.g., maturation step) after step (b). In certain embodiments, the methods provided herein comprises a first step of culturing and expanding a population of hematopoietic cells in a first medium, wherein a plurality of hematopoietic stem or progenitor cells within the hematopoietic cell population differentiate into NK cells. Without wishing to be bound by any parameter, mechanism or theory, culture of the hematopoietic cells as provided herein results in continuous expansion of the hematopoietic cells and differentiation of NK cells from said cells. In certain embodiments, hematopoietic cells, e.g., stem cells or progenitor cells, used in the methods provided herein are expanded and differentiated in the first step using a feeder layer. In other embodiments, hematopoietic cells, e.g., stem cells or progenitor cells, are expanded and differentiated in the first step without the use of a feeder layer. Feeder cell-independent expansion and differentiation of hematopoietic cells can take place in any container compatible with cell culture and expansion, e.g., flask, tube, beaker, dish, multiwell plate, bag or the like. In a specific embodiment, feeder cell-independent expansion of hematopoietic cells takes place in a bag, e.g., a flexible, gas-permeable fluorocarbon culture bag (for example, from American Fluoroseal). In a specific embodiment, the container in which the hematopoietic cells are expanded is suitable for shipping, e.g., to a site such as a hospital or military zone wherein the expanded NK cells are further expanded and differentiated.

In certain embodiments, hematopoietic cells are expanded and differentiated, e.g., in a continuous fashion, in a first culture medium. In one embodiment, the first culture medium is an animal-component free medium. Exemplary animal component-free media useful in the methods provided herein include, but are not limited to, Basal Medium Eagle (BME), Dulbecco's Modified Eagle's Medium (DMEM), Glasgow Minimum Essential Medium (GMEM), Dulbecco's Modified Eagle's Medium/Nutrient Mixture F-12 Ham (DMEM/F-12), Minimum Essential Medium (MEM), Iscove's Modified Dulbecco's Medium (IMDM), Nutrient Mixture F-10 Ham (Ham's F-10), Nutrient Mixture F-12 Ham (Ham's F-12), RPMI-1640 Medium, Williams' Medium E, STEMSPAN® (Cat. No. Stem Cell Technologies, Vancouver, Canada), Glycostem Basal Growth Medium (GBGM®), AIM-V® medium (Invitrogen), X-VIVO™ 10 (Lonza), X-VIVO™ 15 (Lonza), OPT-MIZER (Invitrogen), STEMSPAN® H3000 (STEMCELL Technologies), CELLGRO COMPLETE™ (Mediatech), or any modified variants or combinations thereof.

In preferred embodiments, the first culture medium comprises one or more of medium supplements (e.g., nutrients, cytokines and/or factors). Medium supplements suitable for use in the methods provided herein include, for example without limitation, serum such as human serum AB, fetal bovine serum (FBS) or fetal calf serum (FCS), vitamins, bovine serum albumin (BSA), amino acids (e.g., L-glutamine), fatty acids (e.g., oleic acid, linoleic acid or palmitic acid), insulin (e.g., recombinant human insulin), transferrin (iron saturated human transferrin), .beta.-mercaptoethanol, stem cell factor (SCF), Fms-like-tyrosine kinase 3 ligand (Flt3-L), cytokines such as interleukin-2 (IL-2), interleukin-7 (IL-7), interleukin-15 (IL-15), thrombopoietin (Tpo), heparin, or O-acetyl-carnitine (also referred to as acetylcarnitine, 0-acetyl-L-camitine or OAC). In a specific embodiment, the medium used herein comprises human serum AB. In another specific embodiment, the medium used herein comprises FBS. In another specific embodiment, the medium used herein comprises OAC.

In certain embodiments, the first medium does not comprise one or more of, granulocyte colony-stimulating factor (G-CSF), granulocyte/macrophage colony stimulating factor (GM-CSF), interleukin-6 (IL-6), macrophage inflammatory Protein 1.alpha. (MIP1.alpha.), or leukemia inhibitory factor (LIF).

Thus, in one aspect, provided herein is a two-step method of producing NK cells, wherein said first step comprises expanding and differentiating a population of hematopoietic cells in a first culture medium in the absence of feeder cells, wherein a plurality of hematopoietic cells within said population of hematopoietic cells differentiate into NK cells during said expanding, and wherein the medium comprises SCF at a concentration of about 1 to about 150 ng/mL, IL-2 at a concentration of about 50 to about 1500 IU/mL, IL-7 at a concentration of about 1 to about 150 ng/mL, IL-15 at a concentration 1 to about 150 ng/mL and heparin at a concentration of about 0.1 to about 30 IU/mL, and wherein said SCF, IL-2, IL-7, IL-15 and heparin are not comprised within an undefined component of said medium (e.g., serum). In certain embodiments, said medium comprises one or more of O-acetyl-carnitine (also referred to as acetylcarnitine, O-acetyl-L-camitine or OAC), or a compound that affects acetyl-CoA cycling in mitodronia, thiazovivin, Y-27632, pyintegrin, Rho kinase (ROCK) inhibitors, caspase inhibitors or other anti-apoptotic compounds/peptides, NOVA-RS (Sheffield Bio-Science) or other small-molecule growth enhancers. In certain embodiments, said medium comprises nicotinamide. In certain embodiments, said medium comprises about 0.5 mM-10 mM OAC. In one embodiment, said medium comprises Stemspan® H3000, and/or DMEM:F12 and about 0.5, 1, 2, 3, 4, 5, 6, 7, 8, 9, or 10 mM OAC. In a specific embodiment of the method, said medium is GBGM®. In another specific embodiment, said medium comprises Stemspan® H3000 and about 5 mM of OAC. In another specific embodiment, said medium comprises DMEM:F12 and about 5 mM of OAC. The OAC can be added anytime during the culturing methods provided herein. In certain embodiments, said OAC is added to the first medium and/or during the first culturing step. In some embodiments, said OAC is added to the first medium on Day 0, 1, 2, 3, 4, 5, 6, 7, 8, 9, 10, 11, 12, 13, 14, 15, 16, 17, 18, 19, 20, 21 of the culture. In a specific embodiment, said OAC is added to the first medium on Day 7 of the first culturing step. In a more specific embodiment, said OAC is added to the first medium on Day 7 of the culture and is present throughout the first and second culturing steps. In certain embodiments, said OAC is added to the second medium and/or during the second culturing step. In some embodiments, said OAC is added to the second medium on Day 22, 23, 24, 25, 26, 27, 28, 29, 30, 31, 32, 33, 34, 35 of the culture.

In another specific embodiment, said medium is IMDM supplemented with about 5-20% BSA, about 1-10 .mu.g/mL recombinant human insulin, about 10-50 .mu.g/mL iron saturated human transferrin and about 10-50 .mu.M.beta.-mercaptoethanol. In another specific embodiment, said medium does not comprise one or more, or any, of IL-11, IL-3, homeobox-B4 (HoxB4), and/or methylcellulose. In other specific embodiments, said medium comprises SCF at a concentration of about 0.1 to about 500 ng/mL; about 5 to about 100 ng/mL; or about 20 ng/mL. In other specific embodiments, said medium comprises IL-2 at a concentration of about 10 to about 2000 IU/mL; or about 100 to about 500 IU/mL; or about 200 IU/mL. In other specific embodiments, said medium comprises IL-7 at a concentration of about 0.1 to about 500 ng/mL; about 5 to about 100 ng/mL; or about 20 ng/mL. In other specific embodiments, said medium comprises IL-15 at a concentration of about 0.1 to about 500 ng/mL; about 5 to about 100 ng/mL; or about 10 ng/mL. In other specific embodiments, said medium comprises heparin at concentration of about 0.05 to about 100 U/mL; or about 0.5 to about 20 U/ml; or about 1.5 U/mL. In yet other specific embodiment of the method, said medium further comprises Fms-like-tyrosine kinase 3 ligand (Flt-3 L) at a concentration of about 1 to about 150 ng/mL, thrombopoietin (Tpo) at a concentration of about 1 to about 150 ng/mL, or a combination of both. In other specific embodiments, said medium comprises Flt-3 L at a concentration of about 0.1 to about 500 ng/mL; about 5 to about 100 ng/mL; or about 20 ng/mL. In other specific embodiments, said medium comprises Tpo at a concentration of about 0.1 to about 500 ng/mL; about 5 to about 100 ng/mL; or about 20 ng/mL. In a more specific embodiment of the method, the first culture medium is GBGM®, which comprises about 20 ng/mL SCF, about 20 ng/mL IL-7, about 10 ng/mL IL-15. In another more specific embodiment of the method, the first culture medium is GBGM®, which comprises about 20 ng/mL SCF, about 20 ng/mL Flt3-L, about 200 IU/mL IL-2, about 20 ng/mL IL-7, about 10 ng/mL IL-15, about 20 ng/mL Tpo, and about 1.5 U/mL heparin. In another specific embodiment, said first culture medium further comprises 10% human serum (e.g., human serum AB) or fetal serum (e.g., FBS).

In one embodiment of the invention, a genetically engineered form of (CRISPR)-CRISPR-associated (Cas) protein system [118] of Streptococcus pyogenes is used to induce gene editing of immune checkpoint genes as described for other genes and incorporated by reference [119]. In this system, the type II CRISPR protein Cas9 is directed to genomic target sites by short RNAs, where it functions as an endonuclease. In the naturally occurring system, Cas9 is directed to its DNA target site by two noncoding CRISPR RNAs (crRNAs), including a trans-activating crRNA (tracrRNA) and a precursor crRNA (pre-crRNA). In the synthetically reconstituted system, these two short RNAs can be fused into a single chimeric guide RNA (gRNA). A Cas9 mutant with undetectable endonuclease activity (dCas9) has been targeted to genes in bacteria, yeast, and human cells by gRNAs to silence gene expression through steric hindrance [120].

In one embodiment of the invention, disclosed is the use of a regulatory element that is operably linked to one or more elements of a CRISPR system so as to drive expression of the one or more elements of the CRISPR system, with the goal of manipulating DNA encoding for checkpoint genes in lymphocytes in a manner that prevents lymphocytes from expressing said checkpoint genes. Checkpoint genes relevant for the practice of the invention include: a) the E3 ubiquitin ligase Cbl-b; b) CTLA-4; c) PD-1; d) TIM-3; e) killer inhibitory receptor (KIR); f) LAG-3; g) CD73; h) Fas; i) the aryl hydrocarbon receptor; j) Smad2; k) Smad4; l) TGF-beta receptor; and m) ILT-3. CRISPRs (Clustered Regularly Interspaced Short Palindromic Repeats), also known as SPIDRs (SPacer Interspersed Direct Repeats), constitute a family of DNA loci that are generally unque to a particular bacterial species. The CRISPR locus comprises a distinct class of interspersed short sequence repeats (SSRs) that were recognized in E. coli [121, 122]. The finding of SSRs was not specific to E. Coli in that other groups have identified them in other bacteria such as in tuberculosis [123]. The CRISPR loci differ from other SSRs by the structure of the repeats, which are called short regularly spaced repeats (SRSRs) [124]. Repeats of SRSRs are short elements that occur in clusters that are regularly spaced by unique intervening sequences with a substantially constant length. Although the repeat sequences are highly conserved between strains, the number of interspersed repeats and the sequences of the spacer regions typically differ from strain to strain.

In the embodiment of the invention in which an endogenous CRISPR system is utilized to delete immune checkpoint genes, formation of a CRISPR complex (which is made of a guide sequence hybridized to a target sequence and complexed with one or more Cas proteins) will cause cleavage of one or both strands in or near the target sequence. The tracr sequence used for the practice of the invention may comprise or consist of all or a portion of a wild-type tracr sequence, may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. When inducing gene editing in lymphocytes a Cas enzyme, a guide sequence linked to a tracr-mate sequence, and a tracr sequence could each be operably linked to separate regulatory elements on separate vectors. Useful vectors include viral constructs, which are well known in the art, in one preferred embodiment lentiviral constructs are utilized. In one embodiment of the invention, two or more of the elements expressed from the same or different regulatory elements, may be combined in a single vector, with one or more additional vectors providing any components of the CRISPR system not included in the first vector.

In one embodiment of the invention, CRISPR system elements that are combined in a single vector may be arranged in any suitable orientation, such as one element located 5' with respect to or 3' with respect to a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence, and a tracr sequence embedded within one or more intron sequences. In some embodiments, the CRISPR enzyme, guide sequence, tracr mate sequence, and tracr sequence are operably linked to and expressed from the same promoter.

In one embodiment of the invention, a vector comprises one or more insertion sites, such as a restriction endonuclease recognition sequence. In some embodiments, one or more insertion sites are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell.

In one embodiment, gene deletion of immune checkpoint genes is accomplished using a Cas9 nickase that may be used in combination with guide sequence(s), e.g., two guide sequences, which target respectively sense and antisense strands of the DNA target. This combination allows both strands to be nicked and used to induce NHEJ. In a preferred embodiment, an enzyme coding sequence encoding a CRISPR enzyme is codon optimized for expression in lymphocytes. It is known that the predominance of selected tRNAs in a cell is generally a reflection of the codons used most frequently in peptide synthesis. Accordingly, genes can be tailored for optimal gene expression in a given type of lymphocyte based on codon optimization. Codon usage tables are readily available, for example, at the "Codon Usage Database", and these tables can be adapted in a number of ways [125].

The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art. The guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMNNNNNNNNNNNXGG where NNNNNNNNNNNNXGG (N is A, G, T, or C; and X can be anything) has a single occurrence in the genome. A unique target sequence in a genome may include an *S. pyogenes* Cas9 target site of the form MMMMMMMMMNNNNNNNNNNNXGG where NNNNNNNNNNNXGG (N is A, G, T, or C; and X can be anything) has a single occurrence in the genome. For the *S. thermophilus* CRISPR1 Cas9, a unique target sequence in a genome may include a Cas9 target site of the form MMMMMMMMNNNNNNNNNNNNNXXAGAAW where NNNNNNNNNNNNXXAGAAW (N is A, G, T, or C; X can be anything; and W is A or T) has a single occurrence in the genome. In some embodiments, a guide sequence is selected to reduce the degree of secondary structure within the guide sequence. Secondary structure may be determined by any suitable polynucleotide folding algorithm. A tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence.

In one embodiment of the invention NK cells are utilized as the target cell for gene editing. NK cell expansion methods are widely known in the art, for example, in one methodology NK cells are purified by removing T cells from the cell population, after removal of T cells, the remaining cells are cultured in a medium supplemented with 2500 to 3000 IU/mL of IL-2, and transplanting the NK cells which are amplified from the remaining cells to a patient. The method may comprise a step of removing hematopoietic progenitor cells or other cells from the cell population. In the step of transplanting the NK cells to the patient, the gene edited NK cells may be transplanted together with NK cell progenitors, T cells, NKT cells, hematopoietic progenitor cells or the like. One gene that may be edited is the NK KIR gene. In the method for adoptive immunotherapy of the present invention, the step of transplanting the NK cells to the patient may be implemented by a step of administering the pharmaceutical composition of the present invention to the patient.

In the adoptive immunotherapy method of the present invention, the cell population which is comprised of NK cells may be prepared from at least one kind of cell selected from a group consisting of: hematopoietic stem cells derived from any stem cells selected from a group consisting embryonic stem cells, adult stem cells and induced pluripotent stem cells (iPS cells); hematopoietic stem cells derived from umbilical cord blood; hematopoietic stem cells derived from peripheral blood; hematopoietic stem cells derived from bone marrow blood; umbilical cord blood mononuclear cells; and peripheral blood mononuclear cells. The donor of the cell population which is comprised of NK cells may be the recipient, that is, the patient himself or herself, a blood relative of the patient, or a person who is not a blood relative of the patient. The NK cells may be derived from a donor whose major histocompatibility antigen complex (MHC) and killer immunoglobulin-like receptors (KIR) do not match with those of the recipient. The gene editing step may be performed on NK progenitor cells, thus circumventing the need for wide-scale transfection.

In the amplifying stem of the invention the cell population which is comprised of NK cells may be prepared using various procedures known to those skilled in the art. For example, to collect mononuclear cells from blood such as umbilical cord blood and peripheral blood, the buoyant density separation technique may be employed. NK cells may be collected with immunomagnetic beads. Furthermore, the NK cells may be isolated and identified using a FACS (fluorescent activated cell sorter) or a flow cytometer, following immunofluorescent staining with specific antibodies against cell surface markers. The NK cells may be prepared by separating and removing cells expressing cell surface antigens CD3 and/or CD34, with immunomagnetic beads comprising, but not limited to, Dynabeads (trade mark) manufactured by Dynal and sold by Invitrogen (now Life Technologies Corporation), and CliniMACS (trade mark) of Miltenyi Biotec GmbH. T cells and/or hematopoietic progenitor cells may be selectively injured or killed using specific binding partners for T cells and/or hematopoietic progenitor cells. The step of removing the T cells from the mononuclear cells may be a step of removing cells of other cell types, such as hematopoietic progenitor cells, B cells and/or NKT cells, together with the T cells. The step of removing the hematopoietic progenitor cells from the mononuclear cells may be a step of removing cells of other cell types, such as T cells, B cells and/or NKT cells, together with the hematopoietic progenitor cells. In the amplifying method of the present invention, the mononuclear cells separated from the umbilical cord blood and peripheral blood may be cryopreserved and stored to be thawed in time for transplantation to the patient. Alternatively, the mononuclear cells may be frozen during or after amplification by the method for amplifying the NK cells of the present invention, and thawed in time for transplantation to the patient. Any method known to those skilled in the art may be employed in order to freeze and thaw the blood cells. Any commercially available cryopreservation fluid for cells may be used to freeze the cells.

In one embodiment the invention provides a means of generating a population of cells with tumoricidal ability that have been gene edited. 50 ml of peripheral blood is extracted from a cancer patient and peripheral blood monoclear cells (PBMC) are isolated using the Ficoll Method. PBMC are subsequently resuspended in 10 ml STEM-34 media and allowed to adhere onto a plastic surface for 2-4 hours. The adherent cells are then cultured at 37° C. in STEM-34 media supplemented with 1,000 U/mL granulocyte-monocyte colony-stimulating factor and 500 U/mL IL-4 after non-adherent cells are removed by gentle washing in Hanks Buffered Saline Solution (HBSS). Half of the volume of the GM-CSF and IL-4 supplemented media is changed every other day. Immature DCs are harvested on day 7. In one embodiment said generated DC are used to stimulate T cell and NK cell tumoricidal activity. Specifically, generated DC may be further purified from culture through use of flow cytometry sorting or magnetic activated cell sorting (MACS), or may be utilized as a semi-pure population. Gene editing may be performed prior to coculture, during coculture, or after coculture. In a preferred embodiment gene editing is performed prior to coculture. DC may be added into said patient in need of therapy with the concept of stimulating NK and T cell activity in vivo, or in another embodiment may be incubated in vitro with a population of cells containing T cells and/or NK cells. In one embodiment DC are exposed to agents capable of stimulating maturation in vitro. Specific means of stimulating in vitro maturation include culturing DC or DC containing populations with a toll like receptor agonist. Another means of achieving DC maturation involves exposure of DC to TNF-alpha at a concentration of approximately 20 ng/mL. In order to activate T cells and/or NK cells in vitro, cells are cultured in media containing approximately 1000 IU/ml of interferon gamma. Incubation with interferon gamma may be performed for the period of 2 hours to the period of 7 days. Preferably, incubation is performed for approximately 24 hours, after which T cells and/or NK cells are stimulated via the CD3 and CD28 receptors. One means of accomplishing this is by addition of antibodies capable of activating these receptors. In one embodiment approximately, 2 ug/ml of anti-CD3 antibody is added, together with approximately 1 ug/ml anti-CD28. In order to promote survival of T cells and NK cells, was well as to stimulate proliferation, a T cell/NK mitogen may be used. In one embodiment the cytokine IL-2 is utilized. Specific concentrations of IL-2 useful for the practice of the invention are approximately 500 u/mL IL-2. Media containing IL-2 and antibodies may be changed every 48 hours for approximately 8-14 days. In one particular embodiment DC are included to said T cells and/or NK cells in order to endow cytotoxic activity towards tumor cells. In a particular embodiment, inhibitors of caspases are added in the culture so as to reduce rate of apoptosis of T cells and/or NK cells. Generated cells can be administered to a subject intradermally, intramuscularly, subcutaneously, intraperitoneally, intraarterially, intravenously (including a method performed by an indwelling catheter), intratumorally, or into an afferent lymph vessel. Gene editing means that have utilized transfection of T cells with CRISPR-Cas9 are incorporated by reference [126-130].

In some embodiments, the culture of the cells is performed by starting with purified lymphocyte populations, for example, The step of separating the cell population and cell sub-population containing a T cell can be performed, for example, by fractionation of a mononuclear cell fraction by density gradient centrifugation, or a separation means using the surface marker of the T cell as an index. Subsequently, isolation based on surface markers may be performed. Examples of the surface marker include CD3, CD8 and CD4, and separation methods depending on these surface markers are known in the art. For example, the step can be performed by mixing a carrier such as beads or a culturing container on which an anti-CD8 antibody has been immobilized, with a cell population containing a T cell, and recovering a CD8-positive T cell bound to the carrier. As the beads on which an anti-CD8 antibody has been immobilized, for example, CD8 MicroBeads), Dynabeads M450 CD8, and Eligix anti-CD8 mAb coated nickel particles can be suitably used. This is also the same as in implementation using CD4 as an index and, for example, CD4 MicroBeads, Dynabeads M-450 CD4 can also be used. In some embodiments of the invention, T regulatory cells are depleted before initiation of the culture. Depletion of T regulatory cells may be performed by negative selection by removing cells that express makers such as neuropilin, CD25, CD4, CTLA4, and membrane bound TGF-beta.

Experimentation by one of skill in the art may be performed with different culture conditions in order to generate effector lymphocytes, or cytotoxic cells, that possess both maximal activity in terms of tumor killing, as well as migration to the site of the tumor. For example, the step of culturing the cell population and cell sub-population containing a T cell can be performed by selecting suitable known culturing conditions depending on the cell population. In addition, in the step of stimulating the cell population, known proteins and chemical ingredients, etc., may be added to the medium to perform culturing. For example, cytokines, chemokines or other ingredients may be added to the medium. Herein, the cytokine is not particularly limited as far as it can act on the T cell, and examples thereof include IL-2, IFN-.gamma., transforming growth factor (TGF)-.beta., IL-15, IL-7, IFN-.alpha., IL-12, CD40L, and IL-27. From the viewpoint of enhancing cellular immunity, particularly suitably, IL-2, IFN-.gamma., or IL-12 is used and, from the viewpoint of improvement in survival of a transferred T cell in vivo, IL-7, IL-15 or IL-21 is suitably used. In addition, the chemokine is not particularly limited as far as it acts on the T cell and exhibits migration activity, and examples thereof include RANTES, CCL21, MIP1alpha., MIP1beta., CCL19, CXCL12, IP-10 and MIG. The stimulation of the cell population can be performed by the presence of a ligand for a molecule present on the surface of the T cell, for example, CD3, CD28, or CD44 and/or an antibody to the molecule. Further, the cell population can be stimulated by contacting with other lymphocytes such as antigen presenting cells (dendritic cell) presenting a target peptide such as a peptide derived from a cancer antigen on the surface of a cell. In addition to assessing cytotoxicity and migration as end points, it is within the scope of the current invention to optimize the cellular product based on other means of assessing T cell activity, for example, the function enhancement of the T cell in the method of the present invention can be assessed at a plurality of time points before and after each step using a cytokine assay, an antigen-specific cell assay (tetramer assay), a proliferation assay, a cytolytic cell assay, or an in vivo delayed hypersensitivity test using a recombinant tumor-associated antigen or an immunogenic fragment or an antigen-derived peptide. Examples of an additional method for measuring an increase in an immune response include a delayed hypersensitivity test, flow cytometry using a peptide major histocompatibility gene complex tetramer. a lymphocyte proliferation assay, an enzyme-linked immunosorbent assay, an enzyme-linked immunospot assay, cytokine flow cytometry, a direct cytotoxity assay, measurement of cytokine mRNA by a quantitative reverse transcriptase polymerase chain reaction, or an assay which is currently used for measuring a T cell response such as a limiting dilution method. In vivo assessment of the efficacy of the generated cells using the invention may be assessed in a living body before first administration of the T cell with enhanced function of the present invention, or at various time points after initiation of treatment, using an antigen-specific cell assay, a proliferation assay, a cytolytic cell assay, or an in vivo delayed hypersensitivity test using a recombinant tumor-associated antigen or an immunogenic fragment or an antigen-derived peptide. Examples of an additional method for measuring an increase in an immune response include a delayed hypersensitivity test, flow cytometry using a peptide major histocompatibility gene complex tetramer. a lymphocyte proliferation assay, an enzyme-linked immunosorbent assay, an enzyme-linked immunospot assay, cytokine flow cytometry, a direct cytotoxity assay, measurement of cytokine mRNA by a quantitative reverse transcriptase polymerase chain reaction, or an assay which is currently used for measuring a T cell response such as a limiting dilution method.

Various aspects of the invention relating to the above are enumerated in the following paragraphs:

Aspect 1. A method of inducing an anticancer immune responses comprising the steps of: a) obtaining a cord blood sample; b) isolated mononuclear cells from said cord blood sample; c) culturing said mononuclear cells in a means suitable for gene silencing of an immunological checkpoint; d) continuing said culture in the presence of factors capable of endowing and/or augmenting said cord blood mononuclear cells with tumor cytotoxic activity; and e) administering said cells to a patient in need of treatment.

Aspect 2. The method of aspect 1, wherein said gene silencing comprises induction of RNA interference.

Aspect 3. The method of aspect 2, wherein said RNA interference is induced by administration of short interfering RNA (siRNA).

Aspect 4. The method of aspect 2, wherein said RNA interference is induced by administration of short hairpin RNA.

Aspect 5. The method of aspect 1, wherein said checkpoint is a gene or factor in an immune cell that provides an inhibitory signal to said immune cell's ability to induce an immunological response.

Aspect 6. The method of aspect 5, wherein said immunological response is tumor cytotoxicity.

Aspect 7. The method of aspect 5, wherein said immunological response is cell proliferation.

Aspect 8. The method of aspect 5, wherein said immunological response is expression of CD69.

Aspect 9. The method of aspect 5, wherein said immunological response is expression of CD25.

Aspect 10. The method of aspect 5, wherein said immunological response is expression of perforin.

Aspect 11. The method of aspect 5, wherein said immunological response is expression of granzyme.

Aspect 12. The method of aspect 5, wherein said immunological response is expression of Fas ligand.

Aspect 13. The method of aspect 5, wherein said immunological response is expression of a tumor inhibitory cytokine.

Aspect 14. The method of aspect 13, wherein said tumor inhibitory cytokine induces cell cycle arrest of tumor cells.

Aspect 15. The method of aspect 13, wherein said tumor inhibitory cytokine induces apoptosis of tumor cells.

Aspect 16. The method of aspect 13, wherein said tumor inhibitory cytokine induces autophagy of tumor cells.

Aspect 17. The method of aspect 13, wherein said tumor inhibitory cytokine induces necrosis of tumor cells.

Aspect 18. The method of aspect 13, wherein said tumor inhibitory cytokine induces cell cycle arrest of tumor endothelial cells.

Aspect 19. The method of aspect 13, wherein said tumor inhibitory cytokine induces apoptosis of tumor endothelial cells.

Aspect 20. The method of aspect 13, wherein said tumor inhibitory cytokine induces autophagy of tumor endothelial cells.

Aspect 21. The method of aspect 13, wherein said tumor inhibitory cytokine induces necrosis of tumor endothelial cells.

Aspect 22. The method of aspect 13, wherein said tumor inhibitory cytokine is interferon gamma.

Aspect 23. The method of aspect 13, wherein said tumor inhibitory cytokine is TNF-alpha.

Aspect 24. The method of aspect 13, wherein said tumor inhibitory cytokine is TRAIL.

Aspect 25. The method of aspect 13, wherein said tumor inhibitory cytokine is IL-2.

Aspect 26. The method of aspect 13, wherein said tumor inhibitory cytokine is IL-12.

Aspect 27. The method of aspect 13, wherein said tumor inhibitory cytokine is IL-17.

Aspect 28. The method of aspect 13, wherein said tumor inhibitory cytokine is IL-18.

Aspect 29. The method of aspect 13, wherein said tumor inhibitory cytokine is IL-21.

Aspect 33. The method of aspect 13, wherein said tumor inhibitory cytokine is IL-33.

Aspect 34. The method of aspect 13, wherein said tumor inhibitory cytokine is HMGB1.

Aspect 35. The method of aspect 1, wherein said immunological checkpoint is selected from a group comprising of: a) NR2F6; b) PD-1; c) PD-1L; d) TIM-3; e) CTLA-4; f) CD200; g) STAT6; and h) indolamine 2,3, deoxygenase.

Aspect 36. The method of aspect 1, wherein said factors endowing cord blood with tumor cytotoxic activity are selected from a group comprising of: a) IL-2; b) anti-CD3/anti-CD28 beads; c) IL-7; d) IL-12; e) IL-17; f) IL-15; g) IL-18; and h) IL-33.

Aspect 37. The method of aspect 1, wherein said factors endowing cord blood with tumor cytotoxic activity are toll like receptor activators.

Aspect 38. The method of aspect 37, wherein said toll like receptor is TLR-1.

Aspect 39. The method of aspect 38, wherein said activator of TLR-1 is Pam3CSK4.

Aspect 40. The method of aspect 37, wherein said toll like receptor is TLR-2.

Aspect 41. The method of aspect 40, wherein said activator of TLR-2 is HKLM.

Aspect 42. The method of aspect 37, wherein said toll like receptor is TLR-3.

Aspect 43. The method of aspect 42, wherein said activator of TLR-3 is Poly:IC.

Aspect 44. The method of aspect 37, wherein said toll like receptor is TLR-4.

Aspect 45. The method of aspect 44, wherein said activator of TLR-4 is LPS.

Aspect 46. The method of aspect 44, wherein said activator of TLR-4 is Buprenorphine.

Aspect 47. The method of aspect 44, wherein said activator of TLR-4 is Carbamazepine.

Aspect 48. The method of aspect 44, wherein said activator of TLR-4 is Fentanyl.

Aspect 49. The method of aspect 44, wherein said activator of TLR-4 is Levorphanol.

Aspect 50. The method of aspect 44, wherein said activator of TLR-4 is Methadone.

Aspect 51. The method of aspect 44, wherein said activator of TLR-4 is Cocaine.

Aspect 52. The method of aspect 44, wherein said activator of TLR-4 is Morphine.

Aspect 53. The method of aspect 44, wherein said activator of TLR-4 is Oxcarbazepine.

Aspect 54. The method of aspect 44, wherein said activator of TLR-4 is Oxycodone.

Aspect 55. The method of aspect 44, wherein said activator of TLR-4 is Pethidine.

Aspect 56. The method of aspect 44, wherein said activator of TLR-4 is Glucuronoxylomannan from *Cryptococcus*.

Aspect 57. The method of aspect 44, wherein said activator of TLR-4 is Morphine-3-glucuronide.

Aspect 58. The method of aspect 44, wherein said activator of TLR-4 is lipoteichoic acid.

Aspect 59. The method of aspect 44, wherein said activator of TLR-4 is β-defensin 2.

Aspect 60. The method of aspect 44, wherein said activator of TLR-4 is small molecular weight hyaluronic acid.

Aspect 61. The method of aspect 44, wherein said activator of TLR-4 is fibronectin EDA.

Aspect 62. The method of aspect 44, wherein said activator of TLR-4 is snapin.

Aspect 63. The method of aspect 44, wherein said activator of TLR-4 is tenascin C.

Aspect 64. The method of aspect 37, wherein said toll like receptor is TLR-5.

Aspect 65. The method of aspect 64, wherein said activator of TLR-5 is flagellin.

Aspect 66. The method of aspect 37, wherein said toll like receptor is TLR-6.

Aspect 67. The method of aspect 66, wherein said activator of TLR-6 is FSL-1.

Aspect 68. The method of aspect 37, wherein said toll like receptor is TLR-7.

Aspect 69. The method of aspect 68, wherein said activator of TLR-7 is imiquimod.

Aspect 70. The method of aspect 37, wherein said toll like receptor of TLR-8.

Aspect 71. The method of aspect 70, wherein said activator of TLR8 is ssRNA40/LyoVec.

Aspect 72. The method of aspect 37, wherein said toll like receptor of TLR-9.

Aspect 73. The method of aspect 72, wherein said activator of TLR-9 is a CpG oligonucleotide.

Aspect 74. The method of aspect 72, wherein said activator of TLR-9 is ODN2006.

Aspect 75. The method of aspect 72, wherein said activator of TLR-9 is Agatolimod.

Aspect 76. The method of aspect 1, wherein an antigen presenting cell is added to the culture system.

Aspect 77. The method of aspect 76, wherein said antigen presenting cell is a dendritic cell.

Aspect 78. The method of aspect 77, wherein said dendritic cell is a myeloid dendritic cell.

Aspect 79. The method of aspect 77, wherein said dendritic cell is a lymphoid dendritic cell.

Aspect 80. The method of aspect 76, wherein said antigen presenting cell is a B cell.

Aspect 81. The method of aspect 76, wherein said antigen presenting cell is a neutrophil.

Aspect 82. The method of aspect 76, wherein said antigen presenting cell is an artificial antigen presenting cell.

Aspect 83. The method of aspect 76, wherein said antigen presenting cell is an endothelial cell.

Aspect 84. The method of aspect 76, wherein said antigen presenting cell is activated to enhance immunogenicity.

Aspect 85. The method of aspect 84, wherein said enhanced immunogenicity is augmentation of HLA antigens.

Aspect 86. The method of aspect 84, wherein said enhanced immunogenicity is augmentation of TAP expression.

Aspect 87. The method of aspect 84, wherein said enhanced immunogenicity is augmentation of CD80.

Aspect 88. The method of aspect 84, wherein said enhanced immunogenicity is augmentation of CD86.

Aspect 89. The method of aspect 84, wherein said enhanced immunogenicity is augmentation of IL-12 production.

Aspect 90. The method of aspect 1, wherein said culture additionally consists of soluble inhibitors to immunosuppressive factors.

Aspect 91. The method of aspect 90, wherein said soluble inhibitors are selected from a group comprising of; a) small molecules; and b) antibodies.

Aspect 92. The method of aspect 90, wherein said immunosuppressive factors are selected from a group comprising of: a) HLA-G; b) IL-10; c) indolamine 2,3 deoxygenase; d) cyclo-oxygenases; and e) IL-20.

Aspect 93. The method of aspect 1, wherein a chemotherapeutic agent is administered prior to administration of said therapeutic cells with the intent of reducing tumor burden prior to administration of cellular therapy.

Aspect 94. The method of aspect 93, wherein said immunotherapy is selected from a group comprising of: alkylating agents such as ifosfamide, nimustine hydrochloride, cyclophosphamide, dacarbazine, melphalan, and ranimustine, antimetabolites such as gemcitabine hydrochloride, enocitabine, cytarabine ocfosfate, a cytarabine formulation, tegafur/uracil, a tegafur/gimeracil/oteracil potassium mixture, doxifluridine, hydroxycarbamide, fluorouracil, methotrexate, and mercaptopurine, antitumor antibiotics such as idarubicin hydrochloride, epirubicin hydrochloride, daunorubicin hydrochloride, daunorubicin citrate, doxorubicin hydrochloride, pirarubicin hydrochloride, bleomycin hydrochloride, peplomycin sulfate, mitoxantrone hydrochloride, and mitomycin C, alkaloids such as etoposide, irinotecan hydrochloride, vinorelbine tartrate, docetaxel hydrate, paclitaxel, vincristine sulfate, vindesine sulfate, and vinblastine sulfate, hormone therapy agents such as anastrozole, tamoxifen citrate, toremifene citrate, bicalutamide, flutamide, and estramustine phosphate, platinum complexes such as carboplatin, cisplatin, and nedaplatin, angiogenesis inhibitors such as thalidomide, neovastat, and bevacizumab, L-asparaginase., drugs inhibiting the activity or production of the tumor promoting bioactive substances, such as, for example, antibodies and antibody fragments that neutralize the above bioactive substances, and substances that suppress expression of tumor promoting bioactive substances, such as an siRNA, a ribozyme, an antisense nucleic acid (including RNA, DNA, PNA, and a composite thereof).

Aspect 95. The method of aspect 1, wherein T cells are selectively expanded from cord blood progenitors, said T cells are expanded using the culture of aspect 1, with addition of tumor antigens.

Aspect 96. The method of aspect 95, wherein said tumor antigens are administered in the form of peptides.

Aspect 97. The method of aspect 95, wherein said tumor antigens are administered in the form of proteins.

Aspect 98. The method of aspect 95, wherein said tumor antigens are administered in the form of mRNA encoding said proteins.

Aspect 99. The method of aspect 95, wherein said tumor antigens are administered in the form of DNA encoding said proteins.

Aspect 100. The method of aspect 99, wherein said tumor antigens are selected from a group comprising of: a) Fos-related antigen 1; b) LCK; c) FAP; d) VEGFR2; e) NA17; f) PDGFR-beta; g) PAP; h) MAD-CT-2; i) Tie-2; j) PSA; k) protamine 2; l) legumain; m) endosialin; n) prostate stem cell antigen; o)carbonic anhydrase IX; p) STn; q) Page4; r) proteinase 3; s) GM3 ganglioside; t) tyrosinase; u) MART1; v) gp100; w) SART3; x) RGSS; y) SSX2; z) Globoll; aa) Tn; ab) CEA; ac) hCG; ad) PRAME; ae) XAGE-1; af) AKAP-4; ag) TRP-2; ah) B7H3; ai) sperm fibrous sheath protein; aj) CYP1B1; ak) HMWMAA; al) sLe(a); am) MAGE A1; an) GD2; ao) PSMA; ap) mesothelin; aq) fucosyl GM1; ar) GD3; as) sperm protein 17; at) NY-ESO-1; au) PAXS; av) AFP; aw) polysialic acid; ax) EpCAM; ay) MAGE-A3; az) mutant p53; ba) ras; bb) mutant ras; bc) NY-BR1; bd) PAX3; be) HER2/neu; bf) OY-TES1; bg) HPV E6 E7; bh) PLAC1; bi) hTERT; bj) BORIS; bk) ML-IAP; bl) idiotype of b cell lymphoma or multiple myeloma; bm) EphA2; bn) EGFRvIII; bo) cyclin B1; bp) RhoC; bq) androgen receptor; br) surviving; bs) MYCN; bt) wildtype p53; bu) LMP2; by) ETV6-AML; bw) MUC1; bx) BCR-ABL; by) ALK; bz) WT1; ca) ERG (TMPRSS2 ETS fusion gene); cb) sarcoma translocation breakpoint; cc) STEAP; cd) OFA/iLRP; and ce) Chondroitin sulfate proteoglycan 4 (CSPG4).

Aspect 101. The method of aspect 95, wherein T cells are expanded possessing a Th1 phenotype.

Aspect 102. The method of aspect 101, wherein said Th1 phenotype includes cells expressing markers selected from a group comprising of: a) CD4; b) CD94; c) CD119 (IFNγ R1); d) CD183 (CXCR3); e) CD186 (CXCR6); f) CD191 (CCR1); g) CD195 (CCR5); g) CD212 (IL-12Rβ1&2); h) CD254 (RANKL); i) CD278 (ICOS); j) IL-18R; k) MRP1; l) NOTCH3; and m) TIM3.

Aspect 103. The method of aspect 1, wherein a tumor vaccine is administered in vivo prior to administration of activated cells with the concept of initially establishing a tumor-specific endogenous host response.

Aspect 104. The method of aspect 1, wherein a tumor vaccine is administered in vivo concurrent to administration of activated cells with the concept of initially establishing a tumor-specific endogenous host response.

Aspect 105. The method of aspect 1, wherein a tumor vaccine is administered in vivo subsequent to administration of activated cells with the concept of initially establishing a tumor-specific endogenous host response.

Aspect 106. The method of aspect 1, wherein said cord blood cells are generated as CAR-T cells.

Aspect 107. The method of aspect 1, wherein said cord blood cells are generated as CAR-NK cells.

Aspect 108. The method of aspect 1, wherein hematopoietic precursor cells under a single culturing condition using a medium supplemented with IL-15, SCF, IL-7 and Flt3L are obtained from cord blood; and differentially inducing the cells obtained in the expanding step into NK cells under a culturing condition using a medium supplemented with IL-2.

Aspect 109. The method of aspect 108, wherein the medium used in the step of expanding hematopoietic precursor cells under a single culturing condition is further supplemented with TPO.

Aspect 110. The method of aspect 108, wherein the medium used in each of the steps is supplemented with a human AB-type serum and/or a human serum albumin.

Aspect 111. A method of inducing an anticancer immune responses comprising the steps of: a) obtaining a cord blood sample; b) isolated mononuclear cells from said cord blood sample; c) culturing said mononuclear cells in a means suitable for gene editing of an immunological checkpoint; d) continuing said culture in the presence of factors capable of endowing and/or augmenting said cord blood mononuclear cells with tumor cytotoxic activity; and e) administering said cells to a patient in need of treatment.

Aspect 112. The method of aspect 111, wherein said gene editing is achieved by intracellularly delivering into said lymphocyte a DNA molecule possessing a specific target sequence and encoding the gene product of said target sequence into a non-naturally occurring Clustered Regularly Interspaced Short Palindromic Repeats associated system comprising one or more vectors comprising: a) a first regulatory element that functions in said lymphocyte and is operably linked to at least one nucleotide sequence encoding a CRISPR-Cas system guide RNA that hybridizes with said target sequence, and b) a second regulatory element functioning in a lymphocyte that is operably linked to a nucleotide sequence encoding a Type-II Cas9 protein, wherein components (a) and (b) are located on same or different vectors of the system, whereby the guide RNA targets the sequence whose deletion is desired and the Cas9 protein cleaves the DNA molecule, in a manner such that expression of at least one gene product is substantially inhibited; and in a manner that the Cas9 protein and the guide RNA do not naturally occur together.

Aspect 113. The method of aspect 111, wherein the vectors of the system further comprise one or more nuclear localization signals.

Aspect 114. The method of aspect 111, wherein said guide RNAs comprise a guide sequence fused to a trans-activating cr (tracr) sequence.

Aspect 115. The method of aspect 111, wherein said Cas9 protein is tailored for maximal activity based on DNA codon for said target gene and said lymphocyte.

Aspect 116. The method of aspect 111, wherein said checkpoint is a gene or factor in an immune cell that provides an inhibitory signal to said immune cell's ability to induce an immunological response.

Aspect 117. The method of aspect 116, wherein said immunological response is tumor cytotoxicity.

Aspect 118. The method of aspect 116, wherein said immunological response is cell proliferation.

Aspect 119. The method of aspect 116, wherein said immunological response is expression of CD69.

Aspect 120. The method of aspect 116, wherein said immunological response is expression of CD25.

Aspect 121. The method of aspect 116, wherein said immunological response is expression of perforin.

Aspect 122. The method of aspect 116, wherein said immunological response is expression of granzyme.

Aspect 123. The method of aspect 116, wherein said immunological response is expression of Fas ligand.

Aspect 124. The method of aspect 116, wherein said immunological response is expression of a tumor inhibitory cytokine.

Aspect 125. The method of aspect 124, wherein said tumor inhibitory cytokine induces cell cycle arrest of tumor cells.

Aspect 126. The method of aspect 124, wherein said tumor inhibitory cytokine induces apoptosis of tumor cells.

Aspect 127. The method of aspect 124, wherein said tumor inhibitory cytokine induces autophagy of tumor cells.

Aspect 128. The method of aspect 124, wherein said tumor inhibitory cytokine induces necrosis of tumor cells.

Aspect 129. The method of aspect 124, wherein said tumor inhibitory cytokine induces cell cycle arrest of tumor endothelial cells.

Aspect 130. The method of aspect 124, wherein said tumor inhibitory cytokine induces apoptosis of tumor endothelial cells.

Aspect 131. The method of aspect 124, wherein said tumor inhibitory cytokine induces autophagy of tumor endothelial cells.

Aspect 132. The method of aspect 124, wherein said tumor inhibitory cytokine induces necrosis of tumor endothelial cells.

Aspect 133. The method of aspect 124, wherein said tumor inhibitory cytokine is interferon gamma.

Aspect 134. The method of aspect 124, wherein said tumor inhibitory cytokine is TNF-alpha.

Aspect 135. The method of aspect 124, wherein said tumor inhibitory cytokine is TRAIL.

Aspect 136. The method of aspect 124, wherein said tumor inhibitory cytokine is IL-2.

Aspect 137. The method of aspect 124, wherein said tumor inhibitory cytokine is IL-12.

Aspect 138. The method of aspect 124, wherein said tumor inhibitory cytokine is IL-17.

Aspect 139. The method of aspect 124, wherein said tumor inhibitory cytokine is IL-18.

Aspect 140. The method of aspect 124, wherein said tumor inhibitory cytokine is IL-21.

Aspect 141. The method of aspect 124, wherein said tumor inhibitory cytokine is IL-33.

Aspect 142. The method of aspect 124, wherein said tumor inhibitory cytokine is HMGB1.

Aspect 143. The method of aspect 111, wherein said immunological checkpoint is selected from a group comprising of: a) NR2F6; b) PD-1; c) PD-1L; d) TIM-3; e) CTLA-4; f) CD200; g) STAT6; and h) indolamine 2,3, deoxygenase.

Aspect 144. The method of aspect 111, wherein said factors endowing cord blood with tumor cytotoxic activity are selected from a group comprising of: a) IL-2; b) anti-CD3/anti-CD28 beads; c) IL-7; d) IL-12; e) IL-17; f) IL-15; g) IL-18; and h) IL-33.

Aspect 145. The method of aspect 111, wherein said factors endowing cord blood with tumor cytotoxic activity are toll like receptor activators.

Aspect 146. The method of aspect 111, wherein said immune suppressive checkpoint is selected from a group comprising of: a) the E3 ubiquitin ligase Cbl-b; b) CTLA-4; c) PD-1; d) TIM-3; e) killer inhibitory receptor (KIR); f) LAG-3; g) CD73; h) Fas; i) the aryl hydrocarbon receptor; j) Smad2; k) Smad4; l) TGF-beta receptor; and m) ILT-3.

Aspect 147. The method of aspect 111, wherein said patient is preconditioned with a lymphocyte depleting regimen prior to infusion of said gene edited lymphocytes.

Aspect 148. The method of aspect 111, wherein said lymphocytes are autologous to said patient.

Aspect 149. The method of aspect 111, wherein said lymphocytes are allogeneic to said patient.

Aspect 150. The method of aspect 111, wherein said lymphocytes are chimeric antigen receptor (CAR)-T cells.

Aspect 151. The method of aspect 111, wherein said lymphocytes are transfected with a suicide gene.

Aspect 152. The method of aspect 151, wherein said suicide gene is thymidylate synthase.

Aspect 153. The method of aspect 111, wherein an orally inducible construct is added to said lymphocytes to allow induction of immune stimulatory genes in a controllable manner.

Aspect 154. A cord blood derived allogeneic T cell endowed with enhanced antitumor activity capacity, said T enhanced antitumor activity achieved by inhibition of NR2F6 in said T cell.

Aspect 155. The T cell of aspect 154, wherein said inhibition of NR2F6 is achieved by suppression of mRNA expression.

Aspect 156. The T cell of aspect 154, wherein said inhibition of NR2F6 is achieved by decreasing half life of mRNA expression.

Aspect 157. The T cell of aspect 154, wherein said inhibition of NR2F6 is achieved by treatment with an antisense oligonucleotide.

Aspect 158. The T cell of aspect 157, wherein said antisense oligonucleotide is capable of activating RNAse H to cleave mRNA transcripts specific to NR2F6 mRNA.

Aspect 159. The T cell of aspect 154, wherein inhibition of NR2F6 is achieved by induction of RNA interference.

Aspect 160. The T cell of aspect 159, wherein RNA interference is induced by a molecule capable of inducing RNA interference, said molecule selected from a group comprising of: a) double stranded RNA administered extracellularly; and b) double stranded RNA generated intracellularly.

Aspect 161. The T cell of aspect 160, wherein said molecule capable of inducing RNA interference is delivered to said T cell, through the steps of contacting said cell with a fusion protein-double stranded RNA complex, said complex comprising: a) an RNA molecule comprising a double stranded RNA segment, wherein one of the strands is complementary and the other strand identical to an RNA of NR2F6; and b) a protein, comprising (1) a targeting moiety, which specifically binds to a cell-surface antigen on said T cell, wherein said T cell surface antigen internalizes when the targeting moiety binds the cell surface antigen, and (2) a binding moiety, which binds to double stranded RNA segment, wherein the double stranded RNA segment is delivered to said cell and effects RNA interference of NR2F6 in said T cell.

Aspect 162. The T cell of aspect 161, wherein said T cell antigen is selected from a group comprising of: a) CD3; b) CD4; c) CD7; d) CD8; e) CD28; f) CD30; g) CD40; h) CD45RA; g) CD45RB; h) CD45RO; i) CD62L; j) CD197; k) CD134; l) CD137; and m) CD25.

Aspect 163. The T cell of aspect 161, wherein the double stranded RNA is a short interfering RNA (siRNA).

Aspect 164. The T cell of aspect 161, wherein the targeting moiety is selected from the group comprising of: a) an antibody; b) an antigen binding fragment thereof; c) a single chain antibody; d) a Fab portion of an antibody; and e) Fab2 segment.

Aspect 165. The T cell of aspect 161, wherein the binding moiety is selected from the group comprising of: a) a protamine or a nucleic acid binding fragment thereof; and b) an RNA interference-inducing molecule-binding fragment of protamine.

Aspect 166. The T cell of aspect 161, wherein the binding moiety is a protein or the nucleic acid binding domain of a protein, and the binding moiety is associated with the targeting moiety.

Aspect 167. The T cell of aspect 161, wherein the targeting moiety and binding moiety are comprised as a fusion protein, wherein the binding moiety is fused to the carboxy portion of the targeting moiety.

Aspect 168. The T cell of aspect 161, wherein the binding moiety is a nucleic acid binding domain of a protein selected from the group of nucleic acid binding domains present in proteins selected from the group comprising of: a) GCN4; b) Fos; c) Jun; d) TFIIS; e) FMRI; f) yeast protein HX; g) Vigillin; h) Merl; i) bacterial polynucleotide phosphorylase; j) ribosomal protein S3; and k) a heat shock protein.

Aspect 169. The T cell of aspect 154, wherein said proliferative enhancement is associated with maintenance of telomere length.

Aspect 170. The T cell of aspect 169, wherein said maintenance of telomere length is associated with activation of hTERT.

Aspect 171. The T cell of aspect 154, wherein proliferation of said T cell is induced by signals selected from a group of receptors comprising of: a) CD2; b) CD3; c) CD4; d) CD8; e) IL-2 receptor; f) IL-7 receptor; g) IL-12 receptor; h) TCR; and i) chimeric antigen receptor.

Aspect 172. The T cell of aspect 154, wherein said T cell is a cytotoxic T cell.

Aspect 173. The T cell of aspect 172, wherein said cytotoxic T cell is a CD8 positive T cell.

Aspect 174. The T cell of aspect 172, wherein said cytotoxic T cell is capable of secreting perforin.

Aspect 175. The T cell of aspect 154, wherein said T cell is a helper T cell.

Aspect 176. The T cell of aspect 175, wherein said T cell is a CD4 positive T cell.

Aspect 177. The T cell of aspect 175, wherein said T cell expresses proteins selected from a group comprising of: a) ror-gamma; b) Stat3; c) Stat5; d) Tim-3 and e) Jagged-1.

Aspect 178. The T cell of aspect 154, wherein said T cell is engineered to express a chimeric antigen receptor comprising of: a) an antigen binding domain; b) a transmembrane domain; c) a costimulatory signaling region; and d) and a CD3 zeta signaling domain Aspect 179. The T cell of aspect 178, wherein said antigen binding domain is an antibody or an antigen-binding fragment thereof.

Aspect 180. The T cell of aspect 179, wherein said antigen-binding fragment is a Fab or a scFv.

Aspect 181. The T cell of aspect 179, wherein said antigen-binding domain is a lectin domain expressing protein.

Aspect 182. The T cell of aspect 179, wherein said antigen binding domain binds to a tumor antigen.

Aspect 183. The T cell of aspect 179, wherein said tumor antigen is a molecular marker preferentially associated with cellular proliferation.

Aspect 184. The T cell of aspect 179, wherein said tumor antigen is a molecular marker preferentially associated with cellular proliferation.

Aspect 185. The T cell of aspect 179, wherein said tumor antigen is a molecular marker preferentially associated with cellular apoptosis resistance.

Aspect 186. The T cell of aspect 179, wherein said tumor antigen is a molecular marker preferentially associated with cellular metastasis.

Aspect 187. The T cell of aspect 179, wherein said tumor antigen is associated with a hematologic malignancy.

Aspect 188. The T cell of aspect 179, wherein said tumor antigen is associated with a solid tumor.

Aspect 189. The T cell of aspect 178, wherein said tumor antigen is selected from the group consisting of CD19, CD20, CD22, ROR1, mesothelin, CD33/IL3Ra, c-Met, PSMA, Glycolipid F77, EGFRvIII, GD-2, NY-ESO-1 TCR, MAGE A3 TCR, HER2neu, and any combination thereof.

Aspect 189. The T cell of aspect 178, wherein said costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

Aspect 190. The T cell of aspect 154, wherein said T cell is a naïve T cell.

Aspect 191. The T cell of aspect 154, wherein said T cell is a memory T cell.

Aspect 192. The T cell of aspect 191, wherein said memory T cell is a central memory T cell.

Aspect 193. The T cell of aspect 191, wherein said memory T cell is an effector memory T cell.

Aspect 194. The T cell of aspect 154, wherein said T cell is useful for induction of tumor death subsequent to administration in a human.

Aspect 195. The T cell of aspect 194, wherein said T cell is autologous to the patient to which it is administered.

Aspect 196. The T cell of aspect 194, wherein said T cell is allogeneic to the patient to which it is administered.

Aspect 197. The T cell of aspect 194, wherein said T cell is capable of persisting in a patient for at least week after administration.

Aspect 198. The T cell of aspect 154, wherein said T cell is genetically engineered to express a molecule capable of activating innate immune cells.

Aspect 199. The T cell of aspect 198, wherein said molecule capable of activating innate immune cells is an alarmin.

Aspect 200. The T cell of aspect 199, wherein said alarmin is selected from a group comprising of: a) HMGB1; b) S100A8; c) S100A9; d) S100A12; e) S100B; f) HSP60; g) HSP70; h) beta-defensin; i) LL-37; and j) IL-33.

Aspect 201. The T cell of aspect 198, wherein said molecule capable of activating innate immune system cells is a cytokine.

Aspect 202. The T cell of aspect 201, wherein said cytokine is selected from a group comprising of: a) IL-1; b) IL-6; c) IL-7; d) IL-8; e) IL-12; f) IL-15; g) IL-17; h) IL-17f; i) IL-18; j) IL-21; k) IL-23; l) IL-27; m) IFN-alpha; n) IFN-gamma; o) TNF-alpha; p) IL-15-IL-15 receptor; and q) TRAIL.

Aspect 203. The T cell of aspect 198, wherein said expression of molecule capable of activating innate immune cells is constitutive.

Aspect 204. The T cell of aspect 198, wherein said expression of molecule capable of activating innate immune cells is inducible.

Aspect 205. The T cell of aspect 204, wherein induction of said molecule capable of activating innate immune cells is achieved by transfection of said T cells with a vector comprising a polynucleotide encoding a gene switch, said gene switch comprising (1) at least one transcription factor sequence, wherein said at least one transcription factor sequence encodes a ligand-dependent transcription factor comprising an ecdysone receptor ligand binding domain, operably linked to a promoter, and (2) a polynucleotide encoding a polypeptide at least 85% identical to the wild type innate immune activator polypeptide sequence linked to a promoter which is activated by said ligand-dependent transcription factor wherein following administration of said in vitro engineered T cell to a mammal with cancer, and a first administration of a ligand to said mammal less than 48 hours after said in T cells are administered, wherein said ligand is thereafter administered daily for a period of 2 to 30 days.

Aspect 206. The T cell of aspect 205, wherein said vector is vector selected from a group of vectors comprising of: a) a lentiviral vector; b) adenoviral vector; c) an adeno-associated viral vector.

Aspect 207. The T cell of aspect 205, wherein said polynucleotide encoding a gene switch comprises a first transcription factor sequence and a second transcription factor sequence under the control of a promoter, wherein the proteins encoded by said first transcription factor sequence and said second transcription factor sequence interact to form a protein complex which functions as a ligand-dependent transcription factor.

Aspect 208. The T cell of aspect 207, wherein said first transcription factor and said second transcription factor are connected by an internal ribosomal entry site.

Aspect 209. The T cell of aspect 205, wherein said polynucleotide encoding a gene switch comprises a first transcription factor sequence under the control of a first promoter and a second transcription factor sequence under the control of a second promoter, wherein the proteins encoded by said first transcription factor sequence and said second transcription factor sequence interact to form a protein complex which functions as a ligand-dependent transcription factor.

Aspect 210. The T cell of aspect 205, wherein said ligand is an amidoketone or oxadiazoline.

Aspect 211. The T cell of aspect 205, wherein said polynucleotide sequence encoding a gene switch comprises a polynucleotide sequence encoding a VP-16 transactivation domain.

Aspect 212. The T cell of aspect 205, wherein said polynucleotide sequence encoding a gene switch comprises a polynucleotide sequence encoding a GAL-4 DNA binding domain.

Aspect 213. The T cell of aspect 205, wherein said ecdysone receptor ligand binding domain comprises a substitution mutation.

Aspect 214. The T cell of aspect 205, wherein said ecdysone receptor ligand binding domain is a *Choristoneura fumiferana* ecdysone receptor ligand binding domain.

Aspect 215. The T cell of aspect 205, wherein said polynucleotide sequence encoding a gene switch comprises a polynucleotide sequence encoding an RXR ligand binding domain.

Aspect 216. The T cell of aspect 205, wherein said RXR ligand binding domain is selected from the group consisting of a vertebrate RXR ligand binding domain, an invertebrate RXR ligand binding domain, and a chimeric RXR ligand binding domain.

Aspect 217. The T cell of aspect 205, wherein said vertebrate RXR ligand binding domain is a human RXR ligand binding domain Aspect 218. The T cell of aspect 205, wherein said ligand is a diacylhydrazine.

Aspect 219. The T cell of aspect 205, wherein said mammal is a human; wherein said in vitro engineered T cells are autologous to the patient receiving said T cells; wherein said vector is an adenoviral vector, wherein said polynucleotide encoding a gene switch comprises (1) a first transcription factor sequence encoding a VP-16 transactivation domain and a chimeric RXR ligand binding domain, (2) an EMCV IRES, and (3) a second transcription factor sequence encoding a GAL4 DNA-binding domain and a *Choristoneura fumiferana* ligand binding domain comprising a substitution mutation; wherein said ligand is a diacylhydrazine.

Aspect 220. The T cell of aspect 154, wherein one or more anti-apoptotic genes are transfected in order to enhance ability of said T cell to escape tumor associated T cell apoptosis.

Aspect 221. The T cell of aspect 220, wherein said anti-apoptotic genes are selected from a group comprising of: obestatin, XIAP, survivin, BCL-2, BCL-XL, GATA-4, IGF-1, EGF, heme-oxygenase-1, NF-kB, akt, pi3-k, and epha-2.

Aspect 222. The T cell of aspect 154, wherein T cell in vivo persistence is augmented through transfection of a gene construct capable of inducing RNA interference directed against a molecule associated with induction of apoptosis.

Aspect 223. The T cell of aspect 222, wherein said molecules associated with induction of apoptosis are selected from a group comprising of: Fas, FasL, CASP1 (ICE), CASP10 (MCH4), CASP14, CASP2, CASP3, CASP4, CASP5, CASP6, CASP7, CASP8, CASP9, CFLAR (CASPER), CRADD, PYCARD (TMS1/ASC), ABL1, AKT1, BAD, BAK1, BAX, BCL2L11, BCLAF1, BID, BIK, BNIP3, BNIP3L, CASP1 (ICE), CASP10 (MCH4), CASP14, CASP2, CASP4, CASP6, CASP8, CD70 (TNFSF7), CIDEB, CRADD, FADD, FASLG (TNFSF6), HRK, LTA (TNFB), NOD1 (CARD4), PYCARD (TMS1/ASC), RIPK2, TNF, TNFRSF10A, TNFRSF10B (DR5), TNFRSF25 (DR3), TNFRSF9, TNFSF10 (TRAIL), TNFSF8, TP53, TP53BP2, TRADD, TRAF2, TRAF3, and TRAF4.

Aspect 224. The T cell of aspect 154, wherein said T cell is engineered to stimulate immunity through transfection with an immunomodulatory polypeptide capable of upregulating innate, adaptive or combination thereof of immune responses.

Aspect 225. The T cell of aspect 224, wherein immunomodulatory polypeptide is selected from a group comprising of: ABCF1, BCL6, C3, C4A, CEBPB, CRP, ICEBERG, IL1R1, IL1RN, IL8RB, LTB4R, TOLLIP, IFNA2, IL10RA, IL10RB, IL13, IL13RA1, IL5RA, IL9, IL9R, CD40LG (TNFSF5), IFNA2, IL17C, IL1A, IL1B, IL1F10, IL1F5, IL1F6, IL1F7, IL1F8, IL1F9, IL22, IL5, IL-6, IL8, IL9, IL-18, IL-33, LTA, LTB, MIF, SCYE1, SPP1, TNF, CCL13 (mcp-4), CCR1, CCR2, CCR3, CCR4, CCR5, CCR6, CCR7, CCR8, CCR9, CX3CR1, IL8RA, XCR1 (CCXCR1), C5, CCL1 (1-309), CCL11 (eotaxin), HMGB1, IL-2. IL-12, IL-17, IL33. CCL13 (mcp-4), CCL15 (MIP-1d), CCL16 (HCC-4), CCL17 (TARC), CCL18 (PARC), CCL19, CCL2 (mcp-1), CCL20 (MIP-3a), complement components C3, and C5, 2,3 alpha gal, CCL21 (MIP-2), CCL23 (MPIF-1), CCL24 (MPIF-2/eotaxin-2), CCL25 (TECK), CCL26, CCL3 (MIP-1a), CCL4 (MP-lb), CCL5 (RANTES), CCL7 (mcp-3), CCL8 (mcp-2), CXCL1, CXCL10 (IP-10), CXCL11 (I-TAC/IP-9), CXCL12 (SDF1), CXCL13, CXCL14, CXCL2, CXCL3, CXCL5 (ENA-78/LIX), CXCL6 (GCP-2), CXCL9, IL13, and IL8

Aspect 226. The T cell of aspect 178, wherein said chimeric antigen receptor recognizes a tumor antigen, said tumor antigen is identified by the following steps: a) a plurality of mutant sequences from the nucleic acid of cancer cells from a cancer patient is obtained, said mutant sequences coding for all or a portion of an expressed gene and wherein the mutant sequences each have a mutant position amino acid which substitutes for a wildtype position amino acid located at the same position in the wildtype sequence of the protein, wherein said mutant sequences are obtained using a parallel sequencing platform, said parallel sequencing platform employing parallel processing of said nucleic acid of cancer cells leading to sequence reads and mapping of the sequence reads to a database with reference gene sequences; and b) selecting mutant sequences from those identified in step a) by their ability to induce T cells that are specific for the cancer cells or by their ability to be recognized by patient cancer-specific T cells, wherein cancer antigens for preparing a chimeric antigen receptor, antigen binding domain are identified.

Aspect 227. The T cell of aspect 226, further comprising, prior to step b), identifying an HLA class or supertype of the cancer patient and then selecting an amino acid for said HLA class or supertype as the mutant position amino acid and/or wildtype position amino acid wherein peptides are synthesized and evaluated for activation of T lymphocyte lines prepared from the cancer patient or from an HLA-matched donor, said T lymphocytes obtained by contacting mononuclear cells from the cancer patient or from the HLA-matched donor with cancer cells from the cancer patient.

Aspect 228. The T cell of aspect 226, wherein peptides comprising the selected sequences are evaluated for their ability to bind to HLA histocompatibility antigens prior to testing them in step b).

Aspect 229. The T cell of aspect 228, wherein the ability to bind to HLA histocompatibility antigens is carried out in silico using computer-based algorithm(s) for predicting HLA binding peptides.

Aspect 230. The T cell of aspect 229, wherein said peptides which bind to HLA histocompatibility antigens in silico are synthesized and evaluated for activating T lymphocytes prepared from the cancer patient or from an HLA-matched donor, said T lymphocytes obtained by contacting mononuclear cells from the cancer patient or from the HLA-matched donor with cancer cells from the cancer patient.

Aspect 231. The T cell of aspect 228, wherein the ability to bind to HLA histocompatibility antigens is carried out by synthesizing said peptides and testing them for binding to antigen-presenting cells that express HLA histocompatibility antigens.

Aspect 232. The T cell of aspect 231, wherein said peptides which bind to HLA histocompatibility antigens are synthesized and evaluated for activating T lymphocytes prepared from the cancer patient or from an HLA-matched donor, said T lymphocytes obtained by contacting mononuclear cells from the cancer patient or from the HLA-matched donor with cancer cells from the cancer patient.

Aspect 233. The T cell of aspect 1, wherein said T cell is grown under conditions of sufficient hypoxia to allow self-renewal without significant differentiation.

Aspect 234. The T cell of aspect 154, wherein said T cell is generated from a stem cell.

Aspect 235. The T cell of aspect 234, wherein said stem cell is engineered to lack HLA antigens so as to prevent allogeneic rejection.

Aspect 236. The T cell of aspect 235, wherein said lack of HLA antigens is accomplished by induction of RNA interference.

Aspect 237. The T cell of aspect 234, wherein lack of HLA antigens is accomplished by gene editing.

Aspect 238. The T cell of aspect 237, wherein said stem cell is a pluripotent stem cell.

Aspect 239. The T cell of aspect 238, wherein said pluripotent stem cell is selected from a group comprising of: a) an inducible pluripotent stem cell (iPS); b) an embryonic stem cell; c) a parthenogenic derived stem cell; and d) a somatic cell nuclear transfer generated stem cell.

Aspect 240. The T cell of aspect 234, wherein said stem cell is a dedifferentiated T cell.

Aspect 241. The T cell of aspect 240, wherein said dedifferentiated T cell is a T cell that has been treated with agents capable of inducing chromatin remodeling.

Aspect 242. The T cell of aspect 241, wherein said agents capable of inducing chromatin remodeling are selected from a group comprising of: a) cytoplasm from an undifferentiated cell; b) a histone deacetylase inhibitor; c) a DNA methyltransferase inhibitor; and d) introduction of a pluripotency associated gene.

Aspect 243. The T cell of aspect 242, wherein said histone deacetylase inhibitor is trichostatin A.

Aspect 244. The T cell of aspect 243, wherein trichostatin A is added to culture of T cells at a concentration sufficient to promote upregulation of NANOG expression over 50% compared to control T cells not treated with trichostatin A.

Aspect 245. The T cell of aspect 244, wherein said trichostatin A concentration is 1-1000 ng/ml.

Aspect 246. The T cell of aspect 245, wherein said trichostatin A concentration is 200-700 ng/ml.

Aspect 247. The T cell of aspect 246, wherein said trichostatin A concentration is 100 ng/ml.

Aspect 248. The T cell of aspect 243, wherein said histone deacetylase inhibitor is valproic acid.

Aspect 249. The T cell of aspect 248, wherein said valproic acid is added to said T cells at a concentration sufficient to promote upregulation of Sox-2 expression over 50% compared to control T cells not treated with valproic acid.

Aspect 250. The T cell of aspect 249, wherein said concentration of valproic acid is 2-2000 ng/ml.

Aspect 251. The T cell of aspect 250, wherein said concentration of valproic acid is 300-1000 ng/ml.

Aspect 252. The T cell of aspect 251, wherein said concentration of valproic acid is 300 ng/ml.

Aspect 253. A method of treating a cancer patient comprising the steps of: a) isolating tumor tissue from said cancer patient; b) extracting tumor DNA from said isolated tissue of said cancer patient; c) utilizing a sequencing platform for identifying mutant sequences, said mutant sequences coding for all or a portion of an expressed gene and wherein the mutant sequences each have a mutant position amino acid which substitutes for a wildtype position amino acid located at the same position in the wildtype sequence of the protein, wherein said mutant sequences are obtained using a parallel sequencing platform, said parallel sequencing platform employing parallel processing of said nucleic acid of cancer cells leading to sequence reads and mapping of the sequence reads to a database with reference gene sequences; and d) selecting mutant sequences from those identified in step (c) by their ability to induce T cells that are specific for the cancer cells or by their ability to be recognized by patient cancer-specific T cells; e) synthesizing said mutant sequences; f) utilizing phage display to identifying single chain antibodies recognizing said mutant sequences; and g) inserting said single chain antibody sequences in a chimeric antigen receptor construct, and said construct transfected into a cord blood derived T cell.

Aspect 254. The method of aspect 253, wherein said chimeric antigen receptor comprises of: a) an antigen binding domain; b) a transmembrane domain; c) a costimulatory signaling region; and d) and a CD3 zeta signaling domain Aspect 255. The method of aspect 253, wherein said antigen binding domain is an antibody or an antigen-binding fragment thereof.

Aspect 256. The method aspect 255, wherein said antigen-binding fragment is a Fab or a scFv.

Aspect 257. The method of aspect 255, wherein said antigen-binding domain is a lectin domain expressing protein.

Aspect 258. The method of aspect 255, wherein said antigen binding domain binds to a tumor antigen.

Aspect 259. The method of aspect 255, wherein said tumor antigen is a molecular marker preferentially associated with cellular proliferation.

Aspect 260. The method of aspect 255, wherein said tumor antigen is a molecular marker preferentially associated with cellular proliferation.

Aspect 261. The method of aspect 255, wherein said tumor antigen is a molecular marker preferentially associated with cellular apoptosis resistance.

Aspect 262. The method of aspect 255, wherein said tumor antigen is a molecular marker preferentially associated with cellular metastasis.

Aspect 263. The method of aspect 255, wherein said tumor antigen is associated with a hematologic malignancy.

Aspect 264. The method of aspect 255, wherein said tumor antigen is associated with a solid tumor.

Aspect 265. The method of aspect 253, wherein said T cell is a naïve T cell.

Aspect 266. The method of aspect 253, wherein said T cell is a memory T cell.

Aspect 267. The method of aspect 266, wherein said memory T cell is a central memory T cell.

Aspect 268. The method of aspect 266 of aspect 39, wherein said memory T cell is an effector memory T cell.

Aspect 269. The method of aspect 253, wherein said T cell is useful for induction of tumor death subsequent to administration in a human.

Aspect 270. The method of aspect 253, wherein said T cell is genetically engineered to express a molecule capable of activating innate immune cells.

Aspect 271. The method of aspect 253, wherein said T cell possesses inhibited expression of NR2F6 as compared to a wild-type T cell.

Aspect 272. The method of aspect 271, wherein said inhibition of NR2F6 is achieved by suppression of mRNA expression.

Aspect 273. The method of aspect 271, wherein said inhibition of NR2F6 is achieved by decreasing half life of mRNA expression.

Aspect 274. The method of aspect 271, wherein said inhibition of NR2F6 is achieved by treatment with an antisense oligonucleotide.

Aspect 275. The method of aspect 274, wherein said antisense oligonucleotide is capable of activating RNAse H to cleave mRNA transcripts specific to NR2F6 mRNA.

Aspect 276. The method of aspect 271, wherein inhibition of NR2F6 is achieved by induction of RNA interference.

Aspect 277. The method of aspect 276, wherein RNA interference is induced by a molecule capable of inducing RNA interference, said molecule selected from a group comprising of: a) double stranded RNA administered extracellularly; and b) double stranded RNA generated intracellularly.

REFERENCES

1. Bryceson, Y. T. and H. G. Ljunggren, *Tumor cell recognition by the NK cell activating receptor NKG2D*. Eur J Immunol, 2008. 38(11): p. 2957-61.
2. Waldhauer, I. and A. Steinle, *NK cells and cancer immunosurveillance*. Oncogene, 2008. 27(45): p. 5932-43.
3. Guerra, N., et al., *NKG2D-deficient mice are defective in tumor surveillance in models of spontaneous malignancy*. Immunity, 2008. 28(4): p. 571-80.
4. Guillerey, C., et al., *Immunosurveillance and therapy of multiple myeloma are CD226 dependent*. J Clin Invest, 2015. 125(5): p. 2077-89.
5. Horn, T., et al., *The prognostic effect of tumour-infiltrating lymphocytic subpopulations in bladder cancer*. World J Urol, 2015.

6. de Jong, R. A., et al., *Presence of tumor-infiltrating lymphocytes is an independent prognostic factor in type I and II endometrial cancer.* Gynecol Oncol, 2009. 114(1): p. 105-10.
7. Leffers, N., et al., *Prognostic significance of tumor-infiltrating T-lymphocytes in primary and metastatic lesions of advanced stage ovarian cancer.* Cancer Immunol Immunother, 2009. 58(3): p. 449-59.
8. Coquet, J. M., et al., *Epithelial and dendritic cells in the thymic medulla promote CD4+Foxp3+ regulatory T cell development via the CD27-CD70 pathway.* J Exp Med, 2013. 210(4): p. 715-28.
9. Cowan, J. E., et al., *The thymic medulla is required for Foxp3+ regulatory but not conventional CD4+ thymocyte development.* J Exp Med, 2013. 210(4): p. 675-81.
10. Bautista, J. L., et al., *Intraclonal competition limits the fate determination of regulatory T cells in the thymus.* Nat Immunol, 2009. 10(6): p. 610-7.
11. Ochs, H. D., E. Gambineri, and T. R. Torgerson, *IPEX, FOXP3 and regulatory T-cells: a model for autoimmunity.* Immunol Res, 2007. 38(1-3): p. 112-21.
12. Jie, H. B., et al., *CTLA-4+ Regulatory T Cells Increased in Cetuximab-Treated Head and Neck Cancer Patients Suppress NK Cell Cytotoxicity and Correlate with Poor Prognosis.* Cancer Res, 2015. 75(11): p. 2200-10.
13. Hanakawa, H., et al., *Regulatory T-cell infiltration in tongue squamous cell carcinoma.* Acta Otolaryngol, 2014. 134(8): p. 859-64.
14. Kim, S. T., et al., *Tumor-infiltrating lymphocytes, tumor characteristics, and recurrence in patients with early breast cancer.* Am J Clin Oncol, 2013. 36(3): p. 224-31.
15. Herbst, R. S., et al., *Predictive correlates of response to the anti-PD-L1 antibody MPDL3280A in cancer patients.* Nature, 2014. 515(7528): p. 563-7.
16. Cornetta, K., et al., *Umbilical cord blood transplantation in adults: results of the prospective Cord Blood Transplantation (COBLT).* Biol Blood Marrow Transplant, 2005. 11(2): p. 149-60.
17. Schonberger, S., et al., *Transplantation of haematopoietic stem cells derived from cord blood, bone marrow or peripheral blood: a single centre matched-pair analysis in a heterogeneous risk population.* Klin Padiatr, 2004. 216(6): p. 356-63.
18. Lekakis, L., et al., *Phase II study of unrelated cord blood transplantation for adults with high-risk hematologic malignancies.* Bone Marrow Transplant, 2006. 38(6): p. 421-6.
19. Tomonari, A., et al., *Cord blood transplantation for acute myelogenous leukemia using a conditioning regimen consisting of granulocyte colony-stimulating factor-combined high-dose cytarabine, fludarabine, and total body irradiation.* Eur J Haematol, 2006. 77(1): p. 46-50.
20. Laporte, J. P., et al., *Unrelated mismatched cord blood transplantation in patients with hematological malignancies: a single institution experience.* Bone Marrow Transplant, 1998. 22 Suppl 1: p. S76-7.
21. Sanz, G. F., et al., *Unrelated donor cord blood transplantation in adults with chronic myelogenous leukemia: results in nine patients from a single institution.* Bone Marrow Transplant, 2001. 27(7): p. 693-701.
22. Knutsen, A. P. and D. A. Wall, *Umbilical cord blood transplantation in severe T-cell immunodeficiency disorders: two-year experience.* J Clin Immunol, 2000. 20(6): p. 466-76.
23. Jaing, T. H., et al., *Rapid and complete donor chimerism after unrelated mismatched cord blood transplantation in 5 children with beta-thalassemia major.* Biol Blood Marrow Transplant, 2005. 11(5): p. 349-53.
24. Tomonari, A., et al., *Resolution of Behcet's disease after HLA-mismatched unrelated cord blood transplantation for myelodysplastic syndrome.* Ann Hematol, 2004. 83(7): p. 464-6.
25. Barrangou, R., et al., *CRISPR provides acquired resistance against viruses in prokaryotes.* Science, 2007. 315 (5819): p. 1709-12.
26. Mali, P., et al., *RNA-guided human genome engineering via Cas9.* Science, 2013. 339(6121): p. 823-6.
27. Cho, S. W., et al., *Targeted genome engineering in human cells with the Cas9 RNA-guided endonuclease.* Nat Biotechnol, 2013. 31(3): p. 230-2.
28. Wang, H., et al., *One-step generation of mice carrying mutations in multiple genes by CRISPR/Cas-mediated genome engineering.* Cell, 2013. 153(4): p. 910-8.
29. Theunissen, K. and C. M. Verfaillie, *A multifactorial analysis of umbilical cord blood, adult bone marrow and mobilized peripheral blood progenitors using the improved ML-IC assay.* Exp Hematol, 2005. 33(2): p. 165-72.
30. Ng, Y. Y., et al., *Gene-expression profiling of CD34+ cells from various hematopoietic stem-cell sources reveals functional differences in stem-cell activity.* J Leukoc Biol, 2004. 75(2): p. 314-23.
31. Hogan, C. J., et al., *Engraftment and development of human CD34(+)-enriched cells from umbilical cord blood in NOD/LtSz-scid/scid mice.* Blood, 1997. 90(1): p. 85-96.
32. Sakabe, H., et al., *Human cord blood-derived primitive progenitors are enriched in CD34+c-kit-cells: correlation between long-term culture-initiating cells and telomerase expression.* Leukemia, 1998. 12(5): p. 728-34.
33. Hildbrand, P., et al., *The role of angiopoietins in the development of endothelial cells from cord blood CD34+ progenitors.* Blood, 2004. 104(7): p. 2010-9.
34. Salven, P., et al., *VEGFR-3 and CD133 identify a population of CD34+ lymphatic/vascular endothelial precursor cells.* Blood, 2003. 101(1): p. 168-72.
35. Cho, S. W., et al., *Enhancement of Angiogenic Efficacy of Human Cord Blood Cell Transplantation.* Tissue Eng, 2006.
36. Botta, R., et al., *Heart infarct in NOD-SCID mice: therapeutic vasculogenesis by transplantation of human CD34+ cells and low dose CD34+KDR+ cells.* Faseb J, 2004. 18(12): p. 1392-4.
37. Le Ricousse-Roussanne, S., et al., *Ex vivo differentiated endothelial and smooth muscle cells from human cord blood progenitors home to the angiogenic tumor vasculature.* Cardiovasc Res, 2004. 62(1): p. 176-84.
38. Mayer, H., et al., *Vascular endothelial growth factor (VEGF-A) expression in human mesenchymal stem cells: autocrine and paracrine role on osteoblastic and endothelial differentiation.* J Cell Biochem, 2005. 95(4): p. 827-39.
39. Liu, C. H. and S. M. Hwang, *Cytokine interactions in mesenchymal stem cells from cord blood.* Cytokine, 2005. 32(6): p. 270-9.
40. Gang, E. J., et al., *In vitro endothelial potential of human UC blood-derived mesenchymal stem cells.* Cytotherapy, 2006. 8(3): p. 215-27.
41. De Ugarte, D. A., et al., *Differential expression of stem cell mobilization-associated molecules on multi-lineage cells from adipose tissue and bone marrow.* Immunol Lett, 2003. 89(2-3): p. 267-70.
42. Vaananen, H. K., *Mesenchymal stem cells.* Ann Med, 2005. 37(7): p. 469-79.

43. Knippenberg, M., et al., *Adipose tissue-derived mesenchymal stem cells acquire bone cell-like responsiveness to fluid shear stress on osteogenic stimulation.* Tissue Eng, 2005. 11(11-12): p. 1780-8.
44. Portmann-Lanz, C. B., et al., *Placental mesenchymal stem cells as potential autologous graft for pre-and perinatal neuroregeneration.* Am J Obstet Gynecol, 2006. 194(3): p. 664-73.
45. Zhang, X., et al., *Mesenchymal progenitor cells derived from chorionic villi of human placenta for cartilage tissue engineering.* Biochem Biophys Res Commun, 2006. 340(3): p. 944-52.
46. Shih, D. T., et al., *Isolation and characterization of neurogenic mesenchymal stem cells in human scalp tissue.* Stem Cells, 2005. 23(7): p. 1012-20.
47. Kadivar, M., et al., *In vitro cardiomyogenic potential of human umbilical vein-derived mesenchymal stem cells.* Biochem Biophys Res Commun, 2006. 340(2): p. 639-47.
48. Fu, Y. S., et al., *Conversion of human umbilical cord mesenchymal stem cells in Wharton's jelly to dopaminergic neurons in vitro: potential therapeutic application for Parkinsonism.* Stem Cells, 2006. 24(1): p. 115-24.
49. Tondreau, T., et al., *Mesenchymal stem cells derived from CD133-positive cells in mobilized peripheral blood and cord blood: proliferation, Oct4 expression, and plasticity.* Stem Cells, 2005. 23(8): p. 1105-12.
50. Jeong, J. A., et al., *Rapid neural differentiation of human cord blood-derived mesenchymal stem cells.* Neuroreport, 2004. 15(11): p. 1731-4.
51. Kang, X. Q., et al., *Fibroblast growth factor-4 and hepatocyte growth factor induce differentiation of human umbilical cord blood-derived mesenchymal stem cells into hepatocytes.* World J Gastroenterol, 2005. 11(47): p. 7461-5.
52. Hong, S. H., et al., *In vitro differentiation of human umbilical cord blood-derived mesenchymal stem cells into hepatocyte-like cells.* Biochem Biophys Res Commun, 2005. 330(4): p. 1153-61.
53. Hutson, E. L., S. Boyer, and P. G. Genever, *Rapid isolation, expansion, and differentiation of osteoprogenitors from full-term umbilical cord blood.* Tissue Eng, 2005. 11(9-10): p. 1407-20.
54. Liu, J., et al., *Suppression of human peripheral blood lymphocyte proliferation by immortalized mesenchymal stem cells derived from bone marrow of Banna Minipig inbred-line.* Transplant Proc, 2004. 36(10): p. 3272-5.
55. Togel, F., et al., *Administered mesenchymal stem cells protect against ischemic acute renal failure through differentiation-independent mechanisms.* Am J Physiol Renal Physiol, 2005. 289(1): p. F31-42.
56. Kern, S., et al., *Comparative Analysis of Mesenchymal Stem Cells from Bone Marrow, Umbilical Cord Blood or Adipose Tissue.* Stem Cells, 2006.
57. Zhao, Y., H. Wang, and T. Mazzone, *Identification of stem cells from human umbilical cord blood with embryonic and hematopoietic characteristics.* Exp Cell Res, 2006. 312(13): p. 2454-64.
58. Kogler, G., et al., *A new human somatic stem cell from placental cord blood with intrinsic pluripotent differentiation potential.* J Exp Med, 2004. 200(2): p. 123-35.
59. Zeng, F., et al., *Multiorgan engraftment and differentiation of human cord blood CD34+ Lin-cells in goats assessed by gene expression profiling.* Proc Natl Acad Sci USA, 2006. 103(20): p. 7801-6.
60. Borras, F. E., et al., *Identification of both myeloid CD11c+ and lymphoid CD11c-dendritic cell subsets in cord blood.* Br J Haematol, 2001. 113(4): p. 925-31.
61. Kawano, Y., T. Noma, and J. Yata, *Analysis of decreased autologous mixed lymphocyte reaction of cord blood lymphocytes: with special reference to production of and response to interleukin-2 (IL-2).* Asian Pac J Allergy Immunol, 1984. 2(1): p. 49-55.
62. Petty, R. E. and D. W. Hunt, *Neonatal dendritic cells.* Vaccine, 1998. 16(14-15): p. 1378-82.
63. Sorg, R. V., G. Kogler, and P. Wernet, *Identification of cord blood dendritic cells as an immature CD11c-population.* Blood, 1999. 93(7): p. 2302-7.
64. Han, P., T. McDonald, and G. Hodge, *Potential immaturity of the T-cell and antigen-presenting cell interaction in cord blood with particular emphasis on the CD40-CD40 ligand costimulatory pathway.* Immunology, 2004. 113(1): p. 26-34.
65. Drohan, L., et al., *Selective developmental defects of cord blood antigen-presenting cell subsets.* Hum Immunol, 2004. 65(11): p. 1356-69.
66. De Wit, D., et al., *Impaired responses to toll-like receptor 4 and toll-like receptor 3 ligands in human cord blood.* J Autoimmun, 2003. 21(3): p. 277-81.
67. Mainali, E. S. and J. G. Tew, *Dexamethasone selectively inhibits differentiation of cord blood stem cell derived-dendritic cell (DC) precursors into immature DCs.* Cell Immunol, 2004. 232(1-2): p. 127-36.
68. Wong, O. H., F. P. Huang, and A. K. Chiang, *Differential responses of cord and adult blood-derived dendritic cells to dying cells.* Immunology, 2005. 116(1): p. 13-20.
69. Li, G., Y. J. Kim, and H. E. Broxmeyer, *Macrophage colony-stimulating factor drives cord blood monocyte differentiation into IL-10(high)IL-12absent dendritic cells with tolerogenic potential.* J Immunol, 2005. 174(8): p. 4706-17.
70. Gansuvd, B., et al., *Umbilical cord blood dendritic cells are a rich source of soluble HLA-DR: synergistic effect of exosomes and dendritic cells on autologous or allogeneic T-Cell proliferation.* Hum Immunol, 2003. 64(4): p. 427-39.
71. Kim, S. H., et al., *Exosomes derived from IL-10-treated dendritic cells can suppress inflammation and collagen-induced arthritis.* J Immunol, 2005. 174(10): p. 6440-8.
72. Navarro, V., et al., *The effect of HLA class I (A and B) and class II (DR) compatibility on liver transplantation outcomes: an analysis of the OPTN database.* Liver Transpl, 2006. 12(4): p. 652-8.
73. Gur, H., et al., *Tolerance induction by megadose hematopoietic progenitor cells: expansion of veto cells by short-term culture of purified human CD34(+) cells.* Blood, 2002. 99(11): p. 4174-81.
74. Reisner, Y., et al., *Hematopoietic stem cell transplantation across major genetic barriers: tolerance induction by megadose CD34 cells and other veto cells.* Ann N Y Acad Sci, 2003. 996: p. 72-9.
75. Donckier, V., et al., *Donor stem cell infusion after non-myeloablative conditioning for tolerance induction to HLA mismatched adult living-donor liver graft.* Transpl Immunol, 2004. 13(2): p. 139-46.
76. George, J. F., et al., *An essential role for Fas ligand in transplantation tolerance induced by donor bone marrow.* Nat Med, 1998. 4(3): p. 333-5.
77. Reisner, Y., et al., *Crossing the HLA barriers.* Blood Cells Mol Dis, 2004. 33(3): p. 206-10.
78. Kern, S., et al., *Comparative analysis of mesenchymal stem cells from bone marrow, umbilical cord blood, or adipose tissue.* Stem Cells, 2006. 24(5): p. 1294-301.

79. Deng, W., et al., *Allogeneic bone marrow-derived flk-1+Sca-1-mesenchymal stem cells leads to stable mixed chimerism and donor-specific tolerance*. Exp Hematol, 2004. 32(9): p. 861-7.
80. Kadri, T., et al., *Proteomic study of Galectin-1 expression in human mesenchymal stem cells*. Stem Cells Dev, 2005. 14(2): p. 204-12.
81. Ryan, J. M., et al., *Mesenchymal stem cells avoid allogeneic rejection*. J Inflamm (Lond), 2005. 2: p. 8.
82. Beyth, S., et al., *Human mesenchymal stem cells alter antigen-presenting cell maturation and induce T-cell unresponsiveness*. Blood, 2005. 105(5): p. 2214-9.
83. Aggarwal, S. and M. F. Pittenger, *Human mesenchymal stem cells modulate allogeneic immune cell responses*. Blood, 2005. 105(4): p. 1815-22.
84. Plumas, J., et al., *Mesenchymal stem cells induce apoptosis of activated T cells*. Leukemia, 2005. 19(9): p. 1597-604.
85. Maccario, R., et al., *Interaction of human mesenchymal stem cells with cells involved in alloantigen-specific immune response favors the differentiation of CD4+ T-cell subsets expressing a regulatory/suppressive phenotype*. Haematologica, 2005. 90(4): p. 516-25.
86. Zappia, E., et al., *Mesenchymal stem cells ameliorate experimental autoimmune encephalomyelitis inducing T-cell anergy*. Blood, 2005. 106(5): p. 1755-61.
87. O'Donoghue, K., et al., *Microchimerism in female bone marrow and bone decades after fetal mesenchymal stem-cell trafficking in pregnancy*. Lancet, 2004. 364(9429): p. 179-82.
88. Halbrecht, J., *Fresh and stored placental blood*. Lancet, 1939. 2: p. 1263.
89. Hassall, O., et al., *Umbilical-cord blood for transfusion in children with severe anaemia in under-resourced countries*. Lancet, 2003. 361(9358): p. 678-9.
90. Bhattacharya, N., *Placental umbilical cord whole blood transfusion: a safe and genuine blood substitute for patients of the under-resourced world at emergency*. J Am Coll Surg, 2005. 200(4): p. 557-63.
91. Bhattacharya, N., *Placental umbilical cord whole blood transfusion to combat anemia in the background of tuberculosis and emaciation and its potential role as an immuno-adjuvant therapy for the under-resourced people of the world*. Clin Exp Obstet Gynecol, 2006. 33(2): p. 99-104.
92. Bhattacharya, N., *Placental umbilical cord blood transfusion: A novel method of treatment of patients with malaria in the background of anemia*. Clin Exp Obstet Gynecol, 2006. 33(1): p. 39-43.
93. Bhattacharya, N., *Placental umbilical cord whole blood transfusion to combat anemia in the background of advanced rheumatoid arthritis and emaciation and its potential role as immunoadjuvant therapy*. Clin Exp Obstet Gynecol, 2006. 33(1): p. 28-33.
94. Bhattacharya, N., *A preliminary study of placental umbilical cord whole blood transfusion in under resourced patients with malaria in the background of anaemia*. Malar J, 2006. 5: p. 20.
95. Bhattacharya, N., *A preliminary report of 123 units of placental umbilical cord whole blood transfusion in HIV-positive patients with anemia and emaciation*. Clin Exp Obstet Gynecol, 2006. 33(2): p. 117-21.
96. Bhattacharya, N., *Spontaneous transient rise of CD34 cells in peripheral blood after 72 hours in patients suffering from advanced malignancy with anemia: effect and prognostic implications of treatment with placental umbilical cord whole blood transfusion*. Eur J Gynaecol Oncol, 2006. 27(3): p. 286-90.
97. Ito, K., et al., *Possible mechanisms of immunotherapy for maintaining pregnancy in recurrent spontaneous aborters: analysis of anti-idiotypic antibodies directed against autologous T-cell receptors*. Hum Reprod, 1999. 14(3): p. 650-5.
98. Smith, J. B., et al., *The number of cells used for immunotherapy of repeated spontaneous abortion influences pregnancy outcome*. J Reprod Immunol, 1992. 22(3): p. 217-24.
99. Porter, D. and J. E. Levine, *Graft-versus-host disease and graft-versus-leukemia after donor leukocyte infusion*. Semin Hematol, 2006. 43(1): p. 53-61.
100. Szpakowski, A., et al., *[The influence of paternal lymphocyte immunization on the balance of Th1/Th2 type reactivity in women with unexplained recurrent spontaneous abortion]*. Ginekol Pol, 2000. 71(6): p. 586-92.
101. Hayakawa, S., et al., *Effects of paternal lymphocyte immunization on peripheral Th1/Th2 balance and TCR V beta and V gamma repertoire usage of patients with recurrent spontaneous abortions*. Am J Reprod Immunol, 2000. 43(2): p. 107-15.
102. Marleau, A. M. and N. Sarvetnick, *T cell homeostasis in tolerance and immunity*. J Leukoc Biol, 2005. 78(3): p. 575-84.
103. Hickman, S. P. and L. A. Turka, *Homeostatic T cell proliferation as a barrier to T cell tolerance*. Philos Trans R Soc Lond B Biol Sci, 2005. 360(1461): p. 1713-21.
104. Rosenberg, S. A. and M. E. Dudley, *Cancer regression in patients with metastatic melanoma after the transfer of autologous antitumor lymphocytes*. Proc Natl Acad Sci USA, 2004. 101 Suppl 2: p. 14639-45.
105. Hess, A. D., et al., *Specificity of effector T lymphocytes in autologous graft-versus-host disease: role of the major histocompatibility complex class II invariant chain peptide*. Blood, 1997. 89(6): p. 2203-9.
106. Miura, Y., et al., *Characterization of the T-cell repertoire in autologous graft-versus-host disease (GVHD): evidence for the involvement of antigen-driven T-cell response in the development of autologous GVHD*. Blood, 2001. 98(3): p. 868-76.
107. Maeda, A., et al., *Intravenous infusion of syngeneic apoptotic cells by photopheresis induces antigen-specific regulatory T cells*. J Immunol, 2005. 174(10): p. 5968-76.
108. Lo, Y. M., et al., *Two-way cell traffic between mother and fetus: biologic and clinical implications*. Blood, 1996. 88(11): p. 4390-5.
109. Bianchi, D. W., et al., *Male fetal progenitor cells persist in maternal blood for as long as 27 years postpartum*. Proc Natl Acad Sci USA, 1996. 93(2): p. 705-8.
110. Khosrotehrani, K. and D. W. Bianchi, *Multi-lineage potential of fetal cells in maternal tissue: a legacy in reverse*. J Cell Sci, 2005. 118(Pt 8): p. 1559-63.
111. Johnson, K. L., et al., *Significant fetal cell microchimerism in a nontransfused woman with hepatitis C: Evidence of long-term survival and expansion*. Hepatology, 2002. 36(5): p. 1295-7.
112. Srivatsa, B., et al., *Microchimerism of presumed fetal origin in thyroid specimens from women: a case-control study*. Lancet, 2001. 358(9298): p. 2034-8.
113. Khosrotehrani, K., et al., *Transfer of fetal cells with multilineage potential to maternal tissue*. Jama, 2004. 292(1): p. 75-80.

114. Khosrotehrani, K., et al., *Combined FISH and immunolabeling on paraffin-embedded tissue sections for the study of microchimerism*. Biotechniques, 2003. 34(2): p. 242-4.
115. Khosrotehrani, K. and D. W. Bianchi, *Fetal cell microchimerism: helpful or harmful to the parous woman?* Curr Opin Obstet Gynecol, 2003. 15(2): p. 195-9.
116. Wang, Y., et al., *Fetal cells in mother rats contribute to the remodeling of liver and kidney after injury*. Biochem Biophys Res Commun, 2004. 325(3): p. 961-7.
117. Tan, X. W., et al., *Fetal microchimerism in the maternal mouse brain: a novel population of fetal progenitor or stem cells able to cross the blood-brain barrier?* Stem Cells, 2005. 23(10): p. 1443-52.
118. Jinek, M., et al., *A programmable dual-RNA-guided DNA endonuclease in adaptive bacterial immunity*. Science, 2012. 337(6096): p. 816-21.
119. Cong, L., et al., *Multiplex genome engineering using CRISPR/Cas systems*. Science, 2013. 339(6121): p. 819-23.
120. Qi, L. S., et al., *Repurposing CRISPR as an RNA-guided platform for sequence-specific control of gene expression*. Cell, 2013. 152(5): p. 1173-83.
121. Ishino, Y., et al., *Nucleotide sequence of the iap gene, responsible for alkaline phosphatase isozyme conversion in Escherichia coli, and identification of the gene product*. J Bacteriol, 1987. 169(12): p. 5429-33.
122. Nakata, A., M. Amemura, and K. Makino, *Unusual nucleotide arrangement with repeated sequences in the Escherichia coli K-12 chromosome*. J Bacteriol, 1989. 171(6): p. 3553-6.
123. Groenen, P. M., et al., *Nature of DNA polymorphism in the direct repeat cluster of Mycobacterium tuberculosis; application for* strain *differentiation by a novel typing method*. Mol Microbiol, 1993. 10(5): p. 1057-65.
124. Mojica, F. J., et al., *Biological significance of a family of regularly spaced repeats in the genomes of Archaea, Bacteria and mitochondria*. Mol Microbiol, 2000. 36(1): p. 244-6.
125. Nakamura, Y., T. Gojobori, and T. Ikemura, *Codon usage tabulated from the international DNA sequence databases; its status* 1999. Nucleic Acids Res, 1999. 27(1): p. 292.
126. Matheson, N.J., A. A. Peden, and P. J. Lehner, *Antibody free magnetic cell sorting of genetically modified primary human CD4+ T cells by one-step streptavidin affinity purification*. PLoS One, 2014. 9(10): p. e111437.
127. Meissner, T. B., et al., *Genome editing for human gene therapy*. Methods Enzymol, 2014. 546: p. 273-95.
128. Ebina, H., et al., *A high excision potential of TALENs for integrated DNA of HIV-based lentiviral vector*. PLoS One, 2015. 10(3): p. e0120047.
129. Choi, Y. S. and S. Crotty, *Retroviral vector expression in TCR transgenic CD4(+) T cells*. Methods Mol Biol, 2015. 1291: p. 49-61.
130. Li, C., et al., *Inhibition of HIV-1 infection of primary CD4+ T cells by gene editing of CCR5 using adenovirus-delivered CRISPR/Cas9*. J Gen Virol, 2015.

The invention claimed is:
1. A method of inducing anticancer activity in mononuclear cells comprising the steps of: a) obtaining a cord blood sample; b) isolated mononuclear cells from said cord blood sample; c) culturing said mononuclear cells to induce gene silencing of the NR2F6 immunological checkpoint; and d) continuing said culture in the presence of IL-33 factor capable of endowing and/or augmenting said cord blood mononuclear cells with tumor cytotoxic activity.
2. The method of claim 1, wherein said gene silencing comprises induction of RNA interference.
3. The method of claim 1, wherein an antigen presenting cell is added during culturing.
4. The method of claim 3, wherein said antigen presenting cell is a dendritic cell.
5. The method of claim 3, wherein said antigen presenting cell is activated to enhance immunogenicity.
6. The method of claim 5, wherein said enhanced immunogenicity is augmentation of HLA antigens.
7. The method of claim 1, wherein said culture additionally comprises soluble inhibitors to immunosuppressive factors.
8. The method of claim 7, wherein said soluble inhibitors are selected from the group consisting of: a) small molecules; and b) antibodies.
9. The method of claim 7, wherein said immunosuppressive factor is HLA-G.
10. The method of claim 1, wherein said mononuclear cells are T cells, selectively expanded from cord blood progenitors from the cord blood sample, said T cells are then expanded using the culture of claim 1, with a tumor antigen.
11. The method of claim 10, wherein said tumor antigen is prostate stem cell antigen.
12. The method of claim 1, wherein said mononuclear cells are T cells possessing a Th1 phenotype.
13. The method of claim 12, wherein said Th1 phenotype includes cells expressing the marker.

* * * * *